US012320934B2

(12) United States Patent
Li et al.

(10) Patent No.: US 12,320,934 B2
(45) Date of Patent: *Jun. 3, 2025

(54) DEVICES, SYSTEMS, AND METHODS FOR TIME CORRECTION

(71) Applicant: SHANGHAI UNITED IMAGING MICROELECTRONICS TECHNOLOGY CO., LTD., Shanghai (CN)

(72) Inventors: Zhigang Li, Shanghai (CN); Qingzhong Zhao, Shanghai (CN); Chengzhi Li, Shanghai (CN)

(73) Assignee: SHANGHAI UNITED IMAGING MICROELECTRONICS TECHNOLOGY CO., LTD., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/536,187

(22) Filed: Dec. 11, 2023

(65) Prior Publication Data

US 2024/0125953 A1    Apr. 18, 2024

Related U.S. Application Data

(63) Continuation of application No. 17/659,659, filed on Apr. 18, 2022, now Pat. No. 11,841,472.

(30) Foreign Application Priority Data

Apr. 16, 2021  (CN) .......... 202120785870.X
Jun. 24, 2021  (CN) .......... 202110707579.5

(51) Int. Cl.
G01T 7/00      (2006.01)
A61B 6/03      (2006.01)
(Continued)

(52) U.S. Cl.
CPC ............ *G01T 7/00* (2013.01); *A61B 6/037* (2013.01); *A61B 6/586* (2013.01); *G01T 1/17* (2013.01);
(Continued)

(58) Field of Classification Search
CPC ............ G01T 7/00; A61B 6/037; A61B 6/586
See application file for complete search history.

(56) References Cited

U.S. PATENT DOCUMENTS 8,921,796 B1    12/2014  Arseneau et al.
2010/0074365 A1  3/2010  Ladebeck et al.
(Continued)

FOREIGN PATENT DOCUMENTS

CN    110025329 A    7/2019
CN    111221027 A    6/2020
(Continued)

OTHER PUBLICATIONS

Du et al. "A Time Walk Correction Method for PET Detectors Based on Leading Edge Discriminators", IEEE Transactions on Radiation Plasma Medical Sciences, 1(5): 385-390. (Year: 2017).*
(Continued)

*Primary Examiner* — Dani Fox
*Assistant Examiner* — Casey Bryant
(74) *Attorney, Agent, or Firm* — METIS IP LLC

(57) ABSTRACT

The present disclosure provides devices, systems, and methods for time correction. The device may include a first time measurement component configured to measure a receiving time of a valid signal; a correction component configured to collect correction information for correcting the receiving time of the valid signal; and a processing device configured to determine a corrected receiving time of the valid signal by correcting the receiving time of the valid signal based on the correction information.

18 Claims, 15 Drawing Sheets

(51) Int. Cl.
  *A61B 6/58* (2024.01)
  *G01T 1/17* (2006.01)
  *G01T 1/29* (2006.01)
  *H03M 1/12* (2006.01)
  *H03M 1/50* (2006.01)

(52) U.S. Cl.
  CPC .......... *G01T 1/2985* (2013.01); *H03M 1/124* (2013.01); *H03M 1/50* (2013.01)

(56) References Cited

U.S. PATENT DOCUMENTS

| | | |
|---|---|---|
| 2014/0021356 A1 | 1/2014 | Zwaans et al. |
| 2018/0372890 A1 | 12/2018 | Zhao et al. |
| 2019/0012812 A1 | 1/2019 | Wang et al. |
| 2021/0333422 A1 | 10/2021 | Nutt et al. |
| 2021/0389479 A1* | 12/2021 | Zhao .......................... G01J 1/46 |
| 2024/0036222 A1* | 2/2024 | Xue ........................... G01T 7/00 |

FOREIGN PATENT DOCUMENTS

| | | |
|---|---|---|
| CN | 111568452 A | 8/2020 |
| CN | 111965691 A | 11/2020 |
| CN | 215268238 U | 12/2021 |
| EP | 3529628 B1 | 3/2022 |
| WO | 2011051506 A1 | 5/2011 |
| WO | 2022098394 A1 | 5/2022 |

OTHER PUBLICATIONS

Helmuth Spieler, Fast Timing Methods for Semiconductor Detectors, IEEE Transactions on Nuclear Science, 29(3): 1142-1158, 1982.

"Constant fraction discriminator", Web page <https://en.wikipedia.org/wiki/Constant_fraction_discriminator>, Dec. 13, 2021.

Glenn F. Knoll, Radiation Detection and Measurement, John Wiley & Sons, 2000, 5 pages.

Alberto Gola et al., Analog Circuit for Timing Measurements With Large Area SiPMs Coupled to LYSO Crystals, IEEE Transactions on Nuclear Science, 60(2): 1296-1302, 2013.

Zhu, Xuezhou, Reserarch on the Readout Electronics of Silicon Photomultiplier Array for TOF-PET Application, Dissertation Submitted to Tsinghua University, 2016, 115 pages.

Du, Junwei et al., A Time-Walk Correction Method for PET Detectors Based on Leading Edge Discriminators, IEEE Transactions on Radiation Plasma Medical Sciences, 1(5): 385-390, 2017.

* cited by examiner

DEVICES, SYSTEMS, AND METHODS FOR TIME CORRECTION

CROSS-REFERENCE TO RELATED APPLICATIONS

This application is a continuation of U.S. patent application Ser. No. 17/659,659, filed on Apr. 18, 2022, which claims priority to Chinese Patent Application No. 202120785870.X, filed on Apr. 16, 2021, and Chinese Patent Application No. 202110707579.5, filed on Jun. 24, 2021, the contents of each of which are incorporated herein by reference.

TECHNICAL FIELD

The present disclosure generally relates to signal processing technology, and more particularly, relates to devices, systems, and methods for time correction.

BACKGROUND

A receiving time of a signal often needs to be determined in signal processing, for example, for atmospheric cosmic ray surveys, molecular imaging, etc. However, an accuracy of the measurement of the receiving time is affected by many factors. For example, the signal often includes sub-signals with different amplitudes, or even if the signal includes only one signal or a same type of signal, an amplitude of the signal may fluctuate. During the transmission of the signal, a leading edge with a large amplitude may first reach a leading edge discriminator (LED), and a leading edge with a small amplitude may reach the LED later than the leading edge with the large amplitude. That is, a time walk effect may occur, thereby reducing the accuracy of the measurement. On the other hand, interference signals included in the signal may also reduce the accuracy of the measurement. Therefore, it is desirable to provide devices, systems, and methods for time correction, which can efficiently increase the accuracy of the measurement of the receiving time of the signal.

SUMMARY

In one aspect of the present disclosure, a time correction device is provided.

The time correction device may include a first time measurement component configured to measure a receiving time of a valid signal; a correction component configured to collect correction information for correcting the receiving time of the valid signal; and a processing device configured to determine a corrected receiving time of the valid signal by correcting the receiving time of the valid signal based on the correction information.

In some embodiments, the correction information may include an amplitude and a duration of a target portion of the valid signal.

In some embodiments, the target portion may be a leading edge of the valid signal.

In some embodiments, the correction component may include an amplitude measurement component configured to measure the amplitude of the target portion of the valid signal; and a second time measurement component configured to measure the duration of the target portion of the valid signal.

In some embodiments, to determine a corrected receiving time of the valid signal by correcting the receiving time of the valid signal based on the correction information, the processing device may be configured to determine a correlation coefficient between the amplitude and the duration; determine a correction value based on the correlation coefficient; and determine the corrected receiving time of the valid signal by correcting the receiving time of the valid signal based on the correction value.

In some embodiments, the device may further include a signal amplification component. The signal amplification component may be configured to generate a first amplification signal by amplifying the valid signal and transmit the first amplification signal to the first time measurement component, and generate a second amplification signal by amplifying the valid signal and transmit the second amplification signal to the correction component, wherein the first time measurement component measures the receiving time of the valid signal based on the first amplification signal, and the correction component collects the correction information based on the second amplification signal.

In some embodiments, the signal amplification component may be electrically connected to a photoelectric conversion component, and the photoelectric conversion component may be configured to receive an excitation signal and convert the excitation signal into the valid signal.

In some embodiments, the device may further include a signal filter configured to obtain the valid signal and an interference signal by filtering an input signal.

In some embodiments, to obtain the valid signal and an interference signal by filtering an input signal, the signal filter may be configured to generate a filtered input signal by performing a filtering operation on the input signal; extract a first portion of the filtered input signal as the interference signal, an amplitude of the first portion being larger than a first threshold and smaller than a second threshold; and extract a second portion of the filtered input signal as the valid signal, an amplitude of the second portion being larger than the second threshold, the second threshold being greater than the first threshold.

In some embodiments, the correction information may include a receiving time of the interference signal, and to determine a corrected receiving time of the valid signal, the processing device may be configured to determine a receiving time difference between the valid signal and the interference signal by comparing the receiving time of the interference signal and the receiving time of the valid signal; obtain a corresponding relationship between correction values and receiving time differences between the valid signal and the interference signal; determine a correction value based on the receiving time difference and the corresponding relationship; and determine the corrected receiving time of the valid signal by correcting the receiving time of the valid signal based on the correction value.

In some embodiments, the corresponding relationship may be determined by performing a process including generating at least one emulation effective received signal, wherein each of the at least one emulation effective received signal is generated by superposing an emulation interference signal on an emulation valid signal; for each of the at least one emulation effective received signal, determining a first difference between a receiving time of the corresponding emulation interference signal and a receiving time of the corresponding emulation effective received signal; for each of the at least one emulation effective received signal, determining a second difference between a receiving time of the corresponding emulation valid signal and the receiving time of the corresponding emulation effective received signal; and determining the corresponding relationship based on the first difference and the second difference of each of the at least one emulation effective received signal.

In some embodiments, the correction information may include an intensity of the interference signal, and to determine a corrected receiving time of the valid signal, the processing device may be configured to obtain a corresponding relationship between correction values and intensities of the interference signal; determine a correction value based on the intensity of the interference signal and the corresponding relationship; and determine the corrected receiving time of the valid signal by correcting the receiving time of the valid signal based on the correction value.

In some embodiments, the corresponding relationship may be determined by performing a process including generating at least one emulation effective received signal, wherein each of the at least one emulation effective received signal is generated by superposing an emulation interference signal on an emulation valid signal; for each of the at least one emulation effective received signal, determining an emulation intensity of the corresponding emulation interference signal; for each of the at least one emulation effective received signal, determining a difference between a receiving time of the corresponding emulation effective received signal and a receiving time of the corresponding emulation valid signal; and determining the corresponding relationship based on the emulation intensity and the difference of each of the at least one emulation effective received signal.

In another aspect of the present disclosure, a positron emission tomography (PET) system is provided. The PET system may include a detector module configured to detect a radiation photon emitted from a subject during a PET scan; a photoelectric conversion component configured to convert the radiation photon detected by the detector module into an input signal; a signal processing component configured to generate a valid signal by processing the input signal; and a time correction device configured to determine a corrected receiving time of the valid signal.

In some embodiments, the signal processing component may include a signal filter configured to generate the valid signal by filtering the input signal.

In still another aspect of the present disclosure, a time correction method is provided. The method may be implemented on a computing device having at least one processor and at least one storage device. The method may include measuring a receiving time of a valid signal; collecting correction information for correcting the receiving time of the valid signal; and determining a corrected receiving time of the valid signal by correcting the receiving time of the valid signal based on the correction information.

In some embodiments, the correction information may include an amplitude and a duration of a target portion of the valid signal.

In some embodiments, the target portion may be a leading edge of the valid signal.

In some embodiments, the determining a corrected receiving time of the valid signal by correcting the receiving time of the valid signal based on the correction information may include determining a correlation coefficient between the amplitude and the duration; determining a correction value based on the correlation coefficient; and determining the corrected receiving time of the valid signal by correcting the receiving time of the valid signal based on the correction value.

In some embodiments, the method may further include obtaining the valid signal and an interference signal by filtering an input signal.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections, or assembly of different levels in ascending order. However, the terms may be displaced by another expression if they achieve the same purpose.

Figure 11:
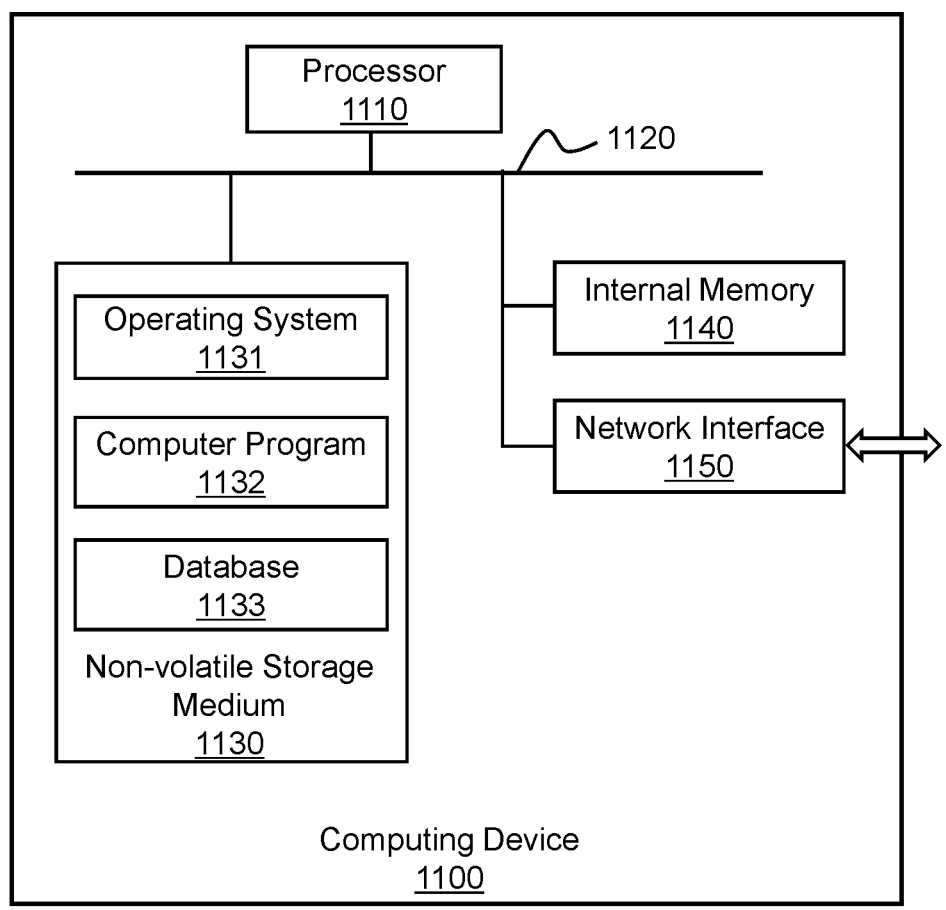
FIG. 11 is a diagram illustrating an exemplary computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage devices. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., a processor 1110 as illustrated in FIG. 11) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included in programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module, or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items. For example, the expression "A and/or B" includes only A, only B, or both A and B. The character "/" includes one of the associated listed terms. The term "multiple" or "a/the plurality of" in the present disclosure refers to two or more. The terms "first," "second," and "third," etc., are used to distinguish similar objects and do not represent a specific order of the objects.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

An aspect of the present disclosure relates to a time correction device. The time correction device may include a time measurement component, a correction component, and a processing device. The time measurement component may be configured to measure a receiving time of a valid signal. The correction component may be configured to collect correction information for correcting the receiving time of the valid signal. The processing device may be configured to determine a corrected receiving time of the valid signal by correcting the receiving time of the valid signal based on the correction information.

Another aspect of the present disclosure relates to a system for imaging. The system may include a positron emission tomography (PET) system. The PET system may include a detector module, a photovoltaic conversion component, a signal processing component, and a time correction device. The detector module may be configured to detect a radiation photon emitted from a subject during a PET scan. The photovoltaic conversion component may be configured to convert the radiation photon detected by the detector module into an input signal. The signal processing component may be configured to generate a valid signal by processing the input signal. The time correction device may be configured to determine a corrected receiving time of the valid signal.

According to the time correction devices of the present disclosure, the correction information may include an amplitude and a duration of a target portion (e.g., a leading edge) of the valid signal. The amplitude and the duration of the target portion may be used to reduce or eliminate the effect of a time walk effect resulted from the amplitude of the valid signal, thereby improving the accuracy of the measurement of the receiving time of the valid signal. Additionally or alternatively, the correction information may include a receiving time of an interference signal and/or an intensity of the interference signal. Therefore, an effect of the interference signal on the receiving time of the valid signal may be reduced or eliminated, which, in turn, improves the accuracy of the measurement of the receiving time of the valid signal. By improving the accuracy of the receiving time of the valid signal, the imaging quality of the PET system including the time correction device may be improved.

Figure 1:
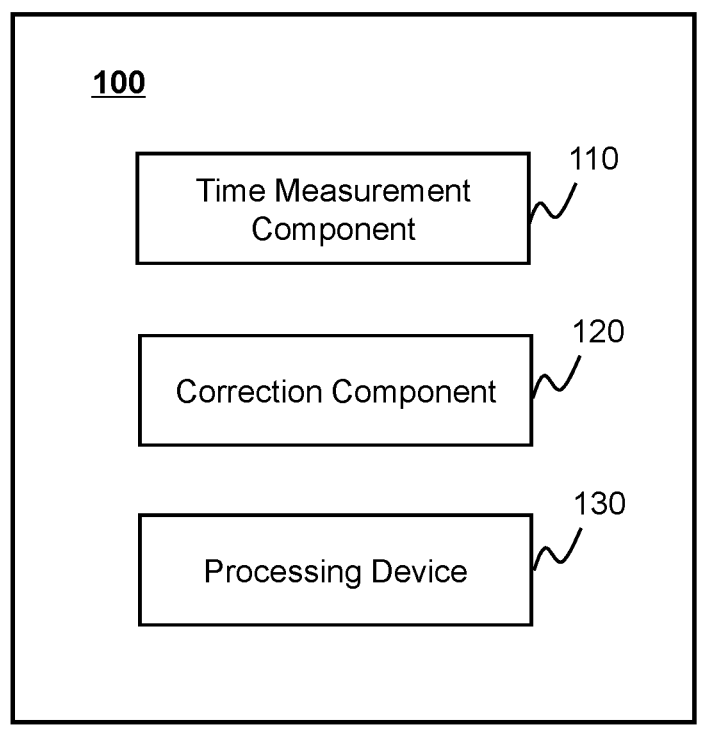
FIG. 1 is a block diagram illustrating an exemplary time correction device according to some embodiments of the present disclosure.

FIG. 1 is a schematic diagram illustrating an exemplary time correction device 100 according to some embodiments of the present disclosure. In some embodiments, the time correction device 100 may be applied in various application scenarios, for example, atmospheric cosmic ray surveys, molecular imaging, etc.

Merely by way of example, the time correction device 100 may be applied in PET imaging. When performing the PET imaging, a radiopharmaceutical (also referred to as a radioactive tracer) may be injected into a subject. Radioactive decay events of the radiopharmaceutical may produce positrons. A positron may interact with a free electron in the tissue of the subject to produce a positron-electron annihilation event and emit two oppositely directed gamma photons. A PET scanner may receive a gamma photon, convert an optical signal of the gamma photon to an electrical signal, and obtain a receiving time of the electrical signal. By disposing the time correction device 100 on the PET scanner, a corrected receiving time of the electrical signal having an improved accuracy may be obtained.

As shown in FIG. 1, the time correction device 100 may include a time measurement component 110, a correction component 120, and a processing device 130.

The time measurement component 110 may be configured to measure a receiving time of a valid signal. The valid signal may include any electrical signal, for example, a voltage signal, a current signal, etc. In some embodiments, the valid signal may refer to a signal including target information. For example, during PET imaging, the valid signal may be a signal including information (e.g., structure information, lesion information, etc.) related to a subject to be imaged. In some embodiments, the valid signal may be an input signal inputted into the time correction device 100. For example, a positron-electron annihilation event may produce gamma photons in PET imaging, and the valid signal may be an input signal obtained by converting an optical signal of a gamma photon.

Alternatively, the valid signal may be generated by performing an interference signal filtering on the input signal. For example, the valid signal and the interference signal may be distinguished from each other based on an amplitude threshold. Merely by way of example, when an amplitude of a signal is larger than or equal to the amplitude threshold, the signal may be determined as a valid signal. The amplitude of the signal may refer to a maximum amplitude value of the signal. When an amplitude of a signal is smaller than the amplitude threshold, the signal may be determined as an interference signal. In some embodiments, the amplitude threshold may be an amplitude value. For example, if the valid signal is a voltage signal, the amplitude threshold may be 1 mV, 2 mV, 5 mV, etc. If the valid signal is a current signal, the amplitude threshold may be 1 mA, 2 mA, 5 mA, etc. In some embodiments, the amplitude threshold may be a ratio. For example, the amplitude threshold may be 1%, 2%, 3%, 5%, etc., of a maximum amplitude of the input signal. In some embodiments, the amplitude threshold may be determined based on system default setting or set manually by a user (e.g., a technician, a doctor, a physicist, etc.).

As used herein, the receiving time of a signal may refer to a moment when an amplitude value of the signal reaches a timing threshold. The timing threshold may refer to an amplitude value at which the signal is regarded as being received. For example, during a transmission process of the signal, an amplitude value of the signal may increase with time. When the amplitude value of the signal reaches the timing threshold, a moment corresponding to the amplitude value may be obtained and designated as the receiving time of the signal. In some embodiments, the timing threshold may be an amplitude value. For example, if the signal is a voltage signal, the timing threshold may be 1 mV, 2 mV, 5 mV, etc. If the signal is a current signal, the timing threshold may be 1 mA, 2 mA, 5 mA, etc. In some embodiments, the timing threshold may be a ratio. For example, the timing threshold may be 1%, 2%, 3%, 5%, etc., of a maximum amplitude of the input signal. In some embodiments, the timing threshold may be determined based on the system default setting or set manually by the user (e.g., a technician, a doctor, a physicist, etc.). In some embodiments, the timing thresholds for different signals may be the same or different. In some embodiments, the timing threshold may be the same as or different from the amplitude threshold as aforementioned.

In some embodiments, the time measurement component 110 may include a timer, a time meter, a chronoscope, a calculagraph, a leading edge discriminator (LED), or the like, or any combination thereof. In some embodiments, the type of the time measurement component 110 may be determined based on actual conditions. For example, the type of the time measurement component 110 may be determined based on a size of the time correction device 100. As another example, the type of the time measurement component 110 may be determined based on an accuracy requirement of the receiving time of the valid signal. Merely by way of example, the time measurement component 110 may include the LED for measuring the receiving time of the valid signal. A measurement accuracy of the LED may be relatively high, thereby improving a measurement accuracy of the time measurement component 110, which, in turn, improves an accuracy of the time correction device 100.

The correction component 120 may be configured to collect correction information for correcting the receiving time of the valid signal. In some embodiments, the correction information may include an intensity and/or a duration of a target portion of the valid signal. As used herein, an intensity of a signal refers to an amplitude and/or an energy of the signal. Merely by way of example, the correction component 120 may include an amplitude measurement component and/or a second time measurement component. The amplitude measurement component may be configured to measure the amplitude of the target portion of the valid signal, and the second time measurement component may be configured to measure the duration of the target portion of the valid signal. More descriptions of the amplitude measurement component and the second time measurement component may be found elsewhere in the present disclosure (e.g., FIGS. 2A-2E and the descriptions thereof).

In some embodiments, the correction information may include a receiving time of the interference signal and/or an intensity of the interference signal. Correspondingly, the correction component 120 may include a third time measurement component and/or an intensity measurement component. The third time measurement component may be configured to measure the receiving time of the interference signal, and the intensity measurement component may be configured to measure the intensity of the interference signal. More descriptions of the correction component may be found elsewhere in the present disclosure (e.g., FIGS. 6A-6B and the descriptions thereof).

The processing device 130 may be configured to process data and/or information obtained from the time measurement component 110 and the correction component 120. In some embodiments, the processing device 130 may determine a corrected receiving time of the valid signal by correcting the receiving time of the valid signal based on the correction information. For example, the processing device 130 may determine the corrected receiving time of the valid signal based on the amplitude and the duration of the target portion of the valid signal. As another example, the processing device 130 may determine the corrected receiving time of the valid signal based on a receiving time difference between the valid signal and the interference signal. As still another example, the processing device 130 may determine the corrected receiving time of the valid signal based on the intensity of the interference signal.

In some embodiments, the processing device 130 may be connected to the time measurement component 110 and the correction component 120, respectively. For example, an input terminal of the processing device 130 may be electrically connected to an output terminal of the time measurement component 110 and an output terminal of the correction component 120, respectively. As another example, the processing device 130 may include a first input terminal and a second input terminal. The first input terminal of the processing device 130 may be electrically connected to an output terminal of the time measurement component 110, and the second input terminal of the processing device 130 may be electrically connected to an output terminal of the correction component 120.

In some embodiments, the processing device 130 may be further configured to output the corrected receiving time of the valid signal. For example, the processing device 130 may be connected to a display device via a wired connection or a wireless connection. After the corrected receiving time is determined, the processing device 130 may transmit the corrected receiving time to the display device for display. As another example, the processing device 130 may be connected to a storage device via a wired connection or a wireless connection. After the corrected receiving time is determined, the processing device 130 may transmit the corrected receiving time to the storage device for storing. In some embodiments, the processing device 130 may be configured to process the corrected receiving time. For example, the processing device 130 may detect an occurrence of an annihilation event based on the corrected receiving time, and reconstruct a PET image of a subject based on the annihilation event.

In some embodiments, the processing device 130 may be a single server or a server group. The server group may be centralized or distributed. In some embodiments, the processing device 130 may be local or remote. For example, the processing device 130 may access information and/or data from the time measurement component 110 and the correction component 120. As another example, the processing device 130 may be directly connected to the time measurement component 110 and the correction component 120 to access information and/or data. In some embodiments, the processing device 130 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing device 130 may be implemented by a computing device 1100 having one or more components as illustrated in FIG. 11.

In some embodiments, the processing device 130 may include one or more hardware processors, such as a microcontroller, a microprocessor, a reduced instruction set computer (RISC), an application-specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field-programmable gate array (FPGA), an advanced RISC machine (ARM), a programmable logic device (PLD), any circuit or processor capable of executing one or more functions, or the like, or any combinations thereof.

Merely for illustration, only one processing device is described in the time correction device 100. However, it should be noted that the time correction device 100 in the present disclosure may also include multiple processing devices. Thus operations and/or method steps that are performed by one processing device as described in the present disclosure may also be jointly or separately performed by the multiple processing devices. For example, if in the present disclosure the processor of the time correction device 100 executes both operation A and operation B, it should be understood that operation A and operation B may also be performed by two or more different processing devices jointly or separately in the time correction device 100 (e.g., a first processing device executes operation A and a second processing device executes operation B, or the first and second processing devices jointly execute operations A and B).

It should be noted that the time correction device 100 is provided for illustration purposes, and not intended to limit the scope of the present disclosure. For persons having ordinary skills in the art, multiple variations and modifications may be made under the teachings of the present disclosure. However, those variations and modifications do not depart from the scope of the present disclosure. For example, the time correction device 100 may further include a storage device configured to store data and/or instructions used for time correction.

Figure 2A:
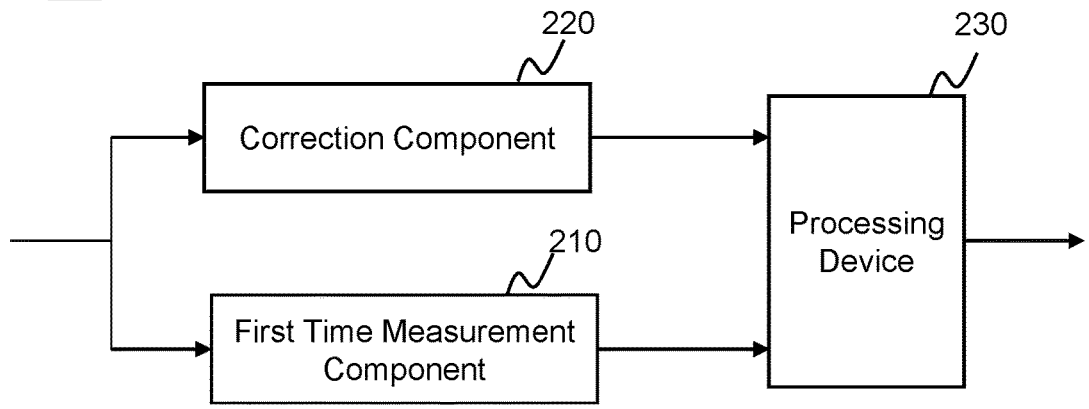
FIG. 2A is a schematic diagram illustrating an exemplary time correction device according to some embodiments of the present disclosure.

FIG. 2A is a schematic diagram illustrating an exemplary time correction device according to some embodiments of the present disclosure.

Conventionally, a receiving time of a valid signal may be measured through a time readout circuit (TRC). The TRC may preamplifier the valid signal, and then determine a leading edge of the valid signal through a leading edge discriminator (LED) so as to achieve timing. However, the valid signal often includes sub-signals with different amplitudes, or even if the valid signal includes only one signal or a same type of signal, an amplitude value of the signal may fluctuate. During the transmission of the valid signal, a leading edge with a large amplitude may first reach the LED, and a leading edge with a small amplitude may reach the LED later than the leading edge with the large amplitude. That is, a time walk effect may occur, which reduces the accuracy of the receiving timing measured by the TRC.

Therefore, a time correction device 200 illustrated in FIG. 2A may be provided according to some embodiments of the present disclosure to reduce or eliminate the time walk effect, thereby improving an accuracy of the measurement of the receiving time of the valid signal.

As shown in FIG. 2A, the time correction device 200 may include a first time measurement component 210, a correction component 220, and a processing device 230.

The valid signal may be transmitted through two channels, wherein a first channel may be transmitted to the correction component 220, and a second channel may be transmitted to the first time measurement component 210. In some embodiments, the first channel of the valid signal may be the same as the second channel of the valid signal. That is, parameters (e.g., an amplitude, a duration, a frequency, etc.) of the first channel of the valid signal may be the same as those of the second channel of the valid signal. For example, after the valid signal is divided into two channels, the first channel of the valid signal may be directly transmitted to the correction component 220, and the second channel of the valid signal may be directly transmitted to the first time measurement component 210. In some embodiments, the first channel of the valid signal may be different from the second channel of the valid signal. That is, at least one of the parameters (e.g., the amplitude, the duration, the frequency, etc.) of the first channel of the valid signal may be different from at least one corresponding parameter of the second channel of the valid signal. For example, after the valid signal is divided into two channels, the first channel of the valid signal may be processed and then transmitted to the correction component 220, and/or the second channel of the valid signal may be processed and then transmitted to the first time measurement component 210. The processing of the first channel or the second channel may include an amplification operation, a leading edge reduction operation, a denoising operation, a transformation operation, a normalization operation, or the like, or any combination thereof. The processing manners of the first channel and the second channel may be different. By the processing the first channel of the valid signal and the second channel of the valid signal with different processing manners, the processed first channel and the processed second channel may be more suitable for their respective subsequent processing, thereby improving the efficiency and the accuracy of the time correction. For the convenience of descriptions, the first channel and the second channel of the valid signal are collectively referred to as the valid signal in the following descriptions.

The first time measurement component 210 may be configured to measure a receiving time of the valid signal based on the second channel of the valid signal. The first time measurement component 210 may be similar to the time measurement component 110 as described in FIG. 1, which is not be repeated herein.

The correction component 220 may be configured to collect correction information for correcting the receiving time of the valid signal based on the first channel of the valid signal. For instance, the correction information may include an amplitude and a duration of a target portion of the valid signal. The target portion of the valid signal may include any portion of the valid signal to be analyzed. Merely by way of example, the target portion may be a leading edge of the valid signal. The amplitude of the leading edge of the valid signal may be a maximum amplitude value of the leading edge of the valid signal. In some embodiments, the amplitude of the valid signal may refer to an intensity of the valid signal. For example, if the valid signal is a voltage signal, the amplitude of the valid signal may be a maximum voltage intensity of the valid signal. As another example, if the valid signal is a current signal, the amplitude of the valid signal may be a maximum current intensity of the valid signal. The duration of the target portion of the valid signal may refer to a time width of the target portion. Merely by way of example, if the target portion is the leading edge, the duration of the target portion may be a time width of an interval in which a value of the valid signal is within a range from a minimum amplitude value (or a value corresponding to a base line) to a maximum amplitude value of the valid signal.

Figure 2B:
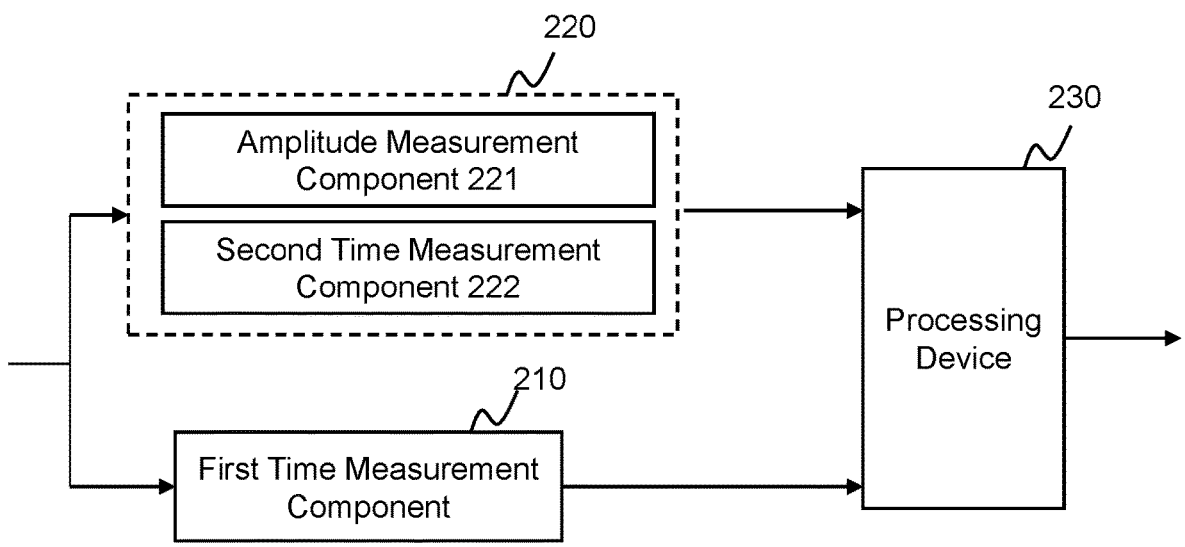
FIG. 2B is a schematic diagram illustrating another exemplary time correction device according to some embodiments of the present disclosure.

In some embodiments, the correction component 220 may include any components that can measure the amplitude and the duration of the target portion of the valid signal, which is not limited in the present disclosure. In some embodiments, the correction component 220 may include an amplitude measurement component 221 and a second time measurement component 222 as shown in FIG. 2B.

The amplitude measurement component 221 may be configured to measure the amplitude of the target portion of the valid signal. For example, the amplitude measurement component 221 may receive the valid signal and measure the amplitude of the leading edge of the valid signal.

In some embodiments, the type of the amplitude measurement component 221 may be determined based on the type of the valid signal. For example, if the valid signal is a digital signal, the amplitude measurement component 221 may include a digital signal processing (DSP) chip, an advanced RISC machines (ARM) chip, etc., for measuring a pulse amplitude (i.e., an amplitude of a digital symbol) of the leading edge of the digital signal. As another example, if the valid signal is an electrical signal (e.g., a voltage signal or a current signal), the amplitude measurement component 221 may include a voltage detector, a current detector, etc., for measuring an amplitude of the electrical signal. As still another example, if the valid signal is an analog signal, the amplitude measurement component 221 may include an analog to digital converter (ADC). The ADC may convert the valid signal (the analog signal) into a digital signal for subsequent data reading and data processing. The ADC may also determine an amplitude of the converted digital signal as the amplitude of the valid signal. In such cases, no additional amplitude measurement component needs to be added into the time correction device 200, thereby simplifying a structure of the time correction device 200 and reducing a manufacturing cost. It should be noted that the descriptions of the amplitude measurement component 221 are merely provided for illustration, and not intended to limit the scope of the present disclosure. For example, the amplitude measurement component 221 may include any devices having an amplitude measurement function.

The second time measurement component 222 may be configured to measure the duration of the target portion of the valid signal. In some embodiments, the second time measurement component 222 may include any devices having a timing function. For example, the second time measurement component 222 may include a pulse timer, a time measurement chip, a time-to-digital converter (TDC), or the like, or any combination thereof. In some embodiments, the second time measurement component 222 may include the TDC. The resolution of the TDC may be relatively higher than other timing devices (e.g., higher than 25 picoseconds (ps)), utilizing the TDC may improve the accuracy of the time correction device 200.

The processing device 230 may be configured to determine a corrected receiving time of the valid signal by correcting the receiving time of the valid signal based on the correction information. For instance, the processing device 230 may obtain the receiving time of the valid signal and the correction information (including the amplitude and the duration of the target portion), determine a correlation coefficient between the amplitude and the duration, determine a correction value based on the correlation coefficient, and determine the corrected receiving time of the valid signal by correcting the receiving time of the valid signal based on the correction value. More descriptions of the determination of the corrected receiving time may be found elsewhere in the present disclosure (e.g., FIGS. 3-4 and the descriptions thereof).

In some embodiments, the processing device 230 may be similar to the processing device 130 as described in connection with FIG. 1. In some embodiments, the processing device 230 may include a TDC. The TDC may include a data processing module for data processing (e.g., determining a correction value). In such cases, the processing device 230 and the second time measurement component 222 may be of the same type, so that the processing device 230 may directly process data (e.g., the duration of the target portion of the valid signal) obtained from the second time measurement component 222 without a format conversion of the data, thereby improving an efficiency of the data processing (e.g., data transmission, data analysis, etc.), which, in turn, improves an efficiency of the time correction device 200.

Figure 2C:
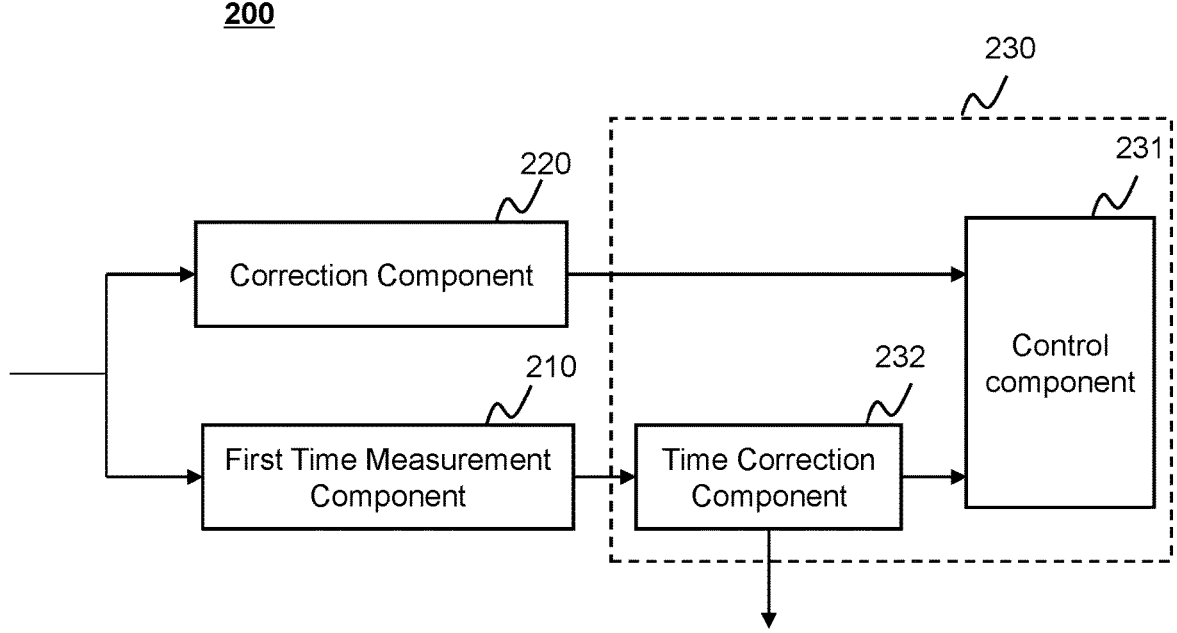
FIG. 2C is a schematic diagram illustrating still another exemplary time correction device according to some embodiments of the present disclosure.

In some embodiments, the processing device 230 may include any components that can process the amplitude and the duration of the target portion of the valid signal and/or correct the receiving time of the valid signal, which is not limited in the present disclosure. In some embodiments, the correction component 220 may include a control component 231 and a time correction component 232 as shown in FIG. 2C.

The control component 231 may be connected to the correction component 220. For example, an input terminal of the control component 231 may be connected to an output terminal of the correction component 220. In some embodiments, the control component 231 may be configured to determine the correlation coefficient between the amplitude and the duration of the target portion, and determine the correction value based on the correlation coefficient. In some embodiments, the control component 231 may include a control circuit, a single chip, a control chip, a micro-unit, etc., which is not limited herein.

The time correction component 232 may be connected to the control component 231 and the first time measurement component 210. For example, the time correction component 232 may include a first input terminal and a second input terminal. The first input terminal of the time correction component 232 may be connected to an output terminal of the control component 231, and the second input terminal may be connected to the output terminal of the first time measurement component 210. In some embodiments, the time correction component 232 may be configured to determine the corrected receiving time of the valid signal by correcting the receiving time of the valid signal based on the correction value.

It should be noted that the time correction device 200 is provided for illustration purposes, and not intended to limit the scope of the present disclosure. For persons having ordinary skills in the art, multiple variations and modifications may be made under the teachings of the present disclosure. However, those variations and modifications do not depart from the scope of the present disclosure.

Figure 2D:
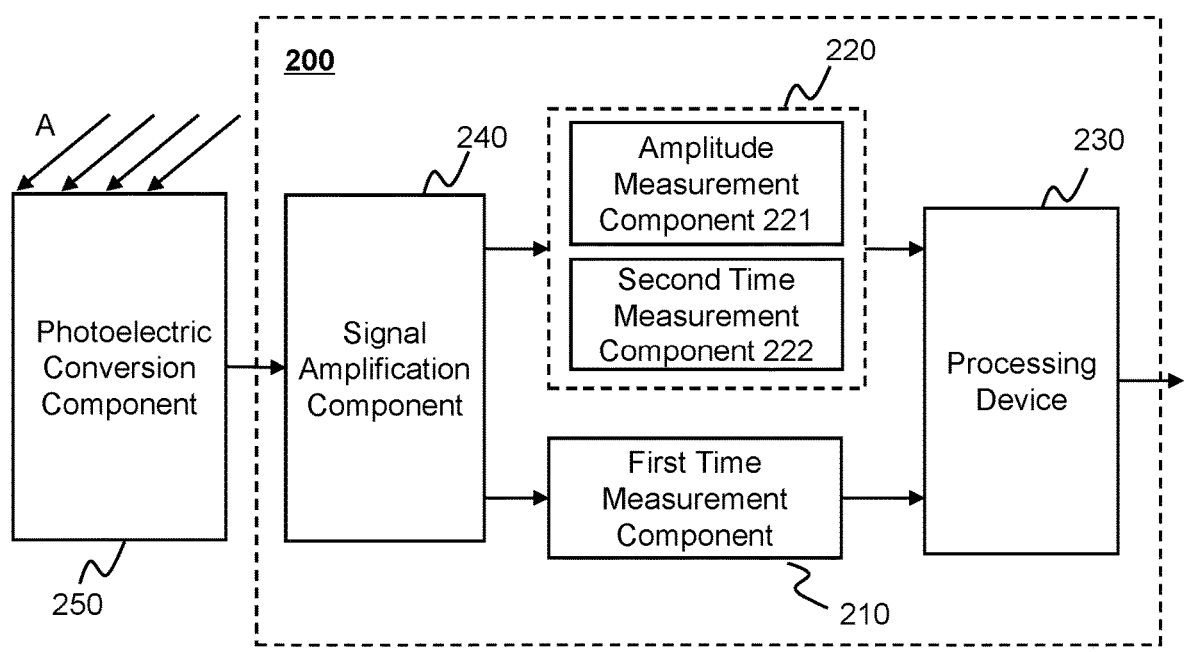
FIG. 2D is a schematic diagram illustrating still another exemplary time correction device according to some embodiments of the present disclosure.

In some embodiments, as shown in FIG. 2D, the time correction device 200 may further include a signal amplification component 240, and the signal amplification component 240 may be connected to a photoelectric conversion component 250. For example, an input terminal of the signal amplification component 240 may be connected to an output terminal of the photoelectric conversion component 250.

The photoelectric conversion component 250 may be configured to receive an excitation signal (e.g., excitation signals A as shown in FIG. 2D) and convert the excitation signal into an input signal for subsequent processing. In some embodiments, the excitation signal may include any rays, for example, a photon, a gamma ray, etc. It should be noted that the excitation signals A are merely provided for illustration, and not intended to limit the scope of the present disclosure. For example, a count (or number), an incidence angle, a contact surface, etc., of the excitation signals A may be altered based on actual conditions. In some embodiments, the photoelectric conversion component 250 may include a Silicon photomultiplier (SiPM), an avalanche photon diode (APD), a photomultiplier tube (PMT), or the like, or any combination thereof.

In some embodiments, the input signal may be processed by a signal processing component to generate the valid signal. For example, the input signal may be filtered to generate the valid signal by a signal filter (not shown in FIG. 2D). Alternatively, the input signal may be directly regarded as the valid signal. The signal amplification component 240 may be configured to receive the valid signal from the photoelectric conversion component 250 and amplify the valid signal. For example, the signal amplification component 240 may generate a first amplification signal by amplifying the valid signal and transmit the first amplification signal to the first time measurement component 210, and generate a second amplification signal by amplifying the valid signal and transmit the second amplification signal to the correction component 220. In some embodiments, an output terminal of the signal amplification component 240 may be connected to the input terminal of the first time measurement component 210 and the input terminal of the correction component 220, respectively.

For example, when an intensity (e.g., an amplitude) of the valid signal is low, the signal amplification component 240 may amplify the valid signal, and transmit the amplification signal(s) (e.g., the first amplification signal and the second amplification signal) to the first time measurement component 210 and the correction component 220, respectively. At this time, the first time measurement component 210 may measure the receiving time of the valid signal based on the first amplification signal, and the correction component 220 may collect the correction information based on the second amplification signal. By amplifying the valid signal, the measurement accuracy of the first time measurement component 210 and/or the correction component 220 may be improved, thereby improving the accuracy of the time correction device 200.

In some embodiments, the signal amplification component 240 may include an analog front end (AFE). The AFE may have advantages including, for example, low input impedance, low noise, high bandwidth, a large dynamic range, etc. The AFE having an excellent dynamic characteristic may be less susceptible to the amplitude fluctuation of the valid signal, thereby effectively improving the measurement reliability and the measurement stability of the first time measurement component 210 and the correction component 220, which, in turn, improves the accuracy of the time correction device 200.

In some embodiments, the AFE may include a charge amplifier, a current buffer, etc. The charge amplifier may be used to amplify the valid signal, so that the first time measurement component 210 and/or the correction component 220 may perform measurement based on the amplified signals easily, thereby improving a sensitivity of the first time measurement component 210 and/or the correction component 220, which, in turn, improves the accuracy and the sensitivity of the time correction device 200. The current buffer may have advantages including, for example, low input impedance, low noise, high bandwidth, a large dynamic range, etc. The current buffer having an excellent dynamic characteristic may be less susceptible to the amplitude fluctuation of the valid signal, thereby effectively improving the measurement reliability and the measurement stability of the first time measurement component 210 and the correction component 220, which, in turn, improves the accuracy of the time correction device 200.

In some embodiments, the time correction device 200 may be used in a PET system. The PET system may include a gantry, a detector component disposed on the gantry, a scanning table, and the time correction device 200. In some embodiments, the detector module may be disposed along a circumference of the gantry, and surround a cylindrical accommodation chamber. The scanning bed may be configured to move along an axial direction of the accommodation chamber. For example, the scanning bed may transmit the subject into or out of the accommodation chamber.

When performing PET imaging, a radiopharmaceutical (also referred to as a radioactive tracer) may be injected into a subject. The radiopharmaceutical may aggregate, with the circulation and metabolism of the subject, in a certain region, for example, cancer lesions, myocardial abnormal tissue, etc. Radioactive decay events of the radiopharmaceutical may produce positrons. A positron may interact with a free electron in the tissue of the subject to produce a positron-electron annihilation event and emit two oppositely directed gamma photons. The detector component of the PET system may receive a gamma photon, and convert an optical signal of the gamma photon to an electrical signal. By disposing the time correction device 200 on the PET system, a receiving time of the electrical signal having an improved accuracy may be obtained. Further, the PET system may determine a difference between receiving times of electrical signals corresponding to the two oppositely directed gamma photons, and then determine an occurrence of the annihilation event based on the difference between the receiving times, thereby determining a lesion position. The determination of the difference between the receiving times of the electrical signals corresponding to the two oppositely directed gamma photons may be referred to as time resolution.

Figure 2E:
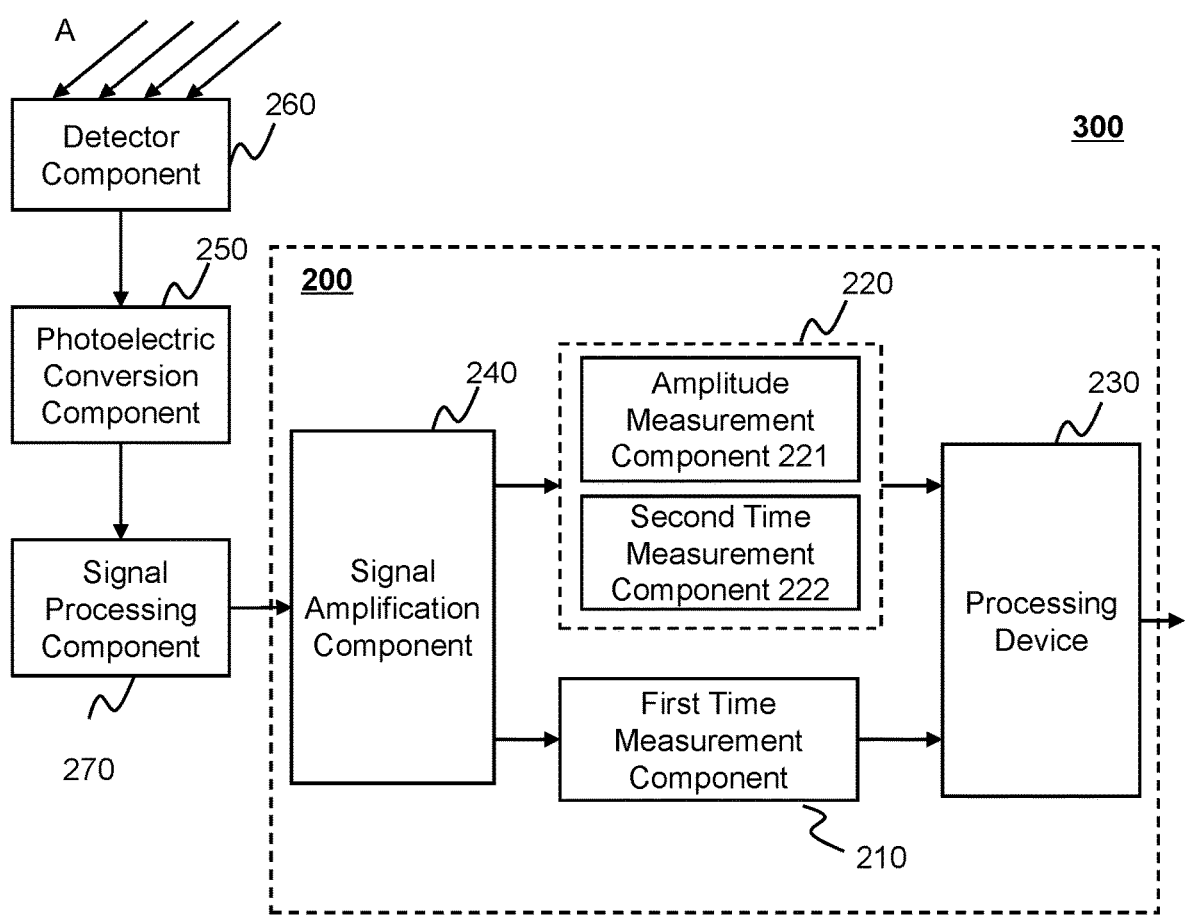
FIG. 2E is a schematic diagram illustrating an exemplary PET system according to some embodiments of the present disclosure.

For illustration purposes, FIG. 2E shows a schematic diagram illustrating an exemplary PET system 300 according to some embodiments of the present disclosure. As shown in FIG. 2E, the PET system 300 may include a detector component 260, the photoelectric conversion component 250, a signal processing component 270, and the time correction device 200.

The detector component 260 may be configured to detect a radiation photon (or referred to as an excitation signal) emitted from a subject during a PET scan. The photovoltaic conversion component 250 may convert an optical signal of the radiation photon into an input signal and transmit the signal to the signal processing component 270.

The signal processing component 270 may be configured to generate a valid signal by processing the input signal. For example, the signal processing component 270 may perform signal processing operation(s) including a filtering operation, a leading edge reduction operation, a denoising operation, a transformation operation, a normalization operation, or the like, or any combination thereof, to generate the valid signal. For example, the signal processing component 270 may include a signal filter configured to filter out an interference signal from the input signal to generate the valid signal. In some embodiments, the signal processing component 270 may be omitted, and the input signal may be designated as the valid signal directly.

The time correction device 200 may be configured to determine a corrected receiving time of the valid signal. More descriptions of the time correction device 200 may be found elsewhere in the present disclosure (e.g., FIGS. 2A-2D and the descriptions thereof).

By disposing the time correction device 200 in the PET system 300, the receiving time of the valid signal may be corrected, thereby improving the detection accuracy of annihilation events, which, in turn, improves the imaging quality of the PET scan.

It should be noted that the PET system 300 is provided for illustration purposes, and not intended to limit the scope of the present disclosure. For persons having ordinary skills in the art, multiple variations and modifications may be made under the teachings of the present disclosure. However, those variations and modifications do not depart from the scope of the present disclosure. For example, the PET system 300 may include more than one detector component 260, more than one photoelectric conversion component 250, and/or more than one time correction device 200.

In some embodiments, the time correction device 200 may be applied to other scenarios, such as, a medical imaging system other than the PET system 300, a system for atmospheric cosmic ray surveys, a time circuit, a time chip, a timer, a timing device, etc., for reducing or eliminating the time walk effect and/or improving an accuracy of timing. Exemplary other medical imaging systems may include a magnetic resonance imaging (MRI) system, a positron emission tomography-computed tomography (PET-CT) system, a positron emission tomography-magnetic resonance (PET-MR) system, a single photon emission computed tomography-computed tomography (SPECT-CT) system, etc.

Figure 3:
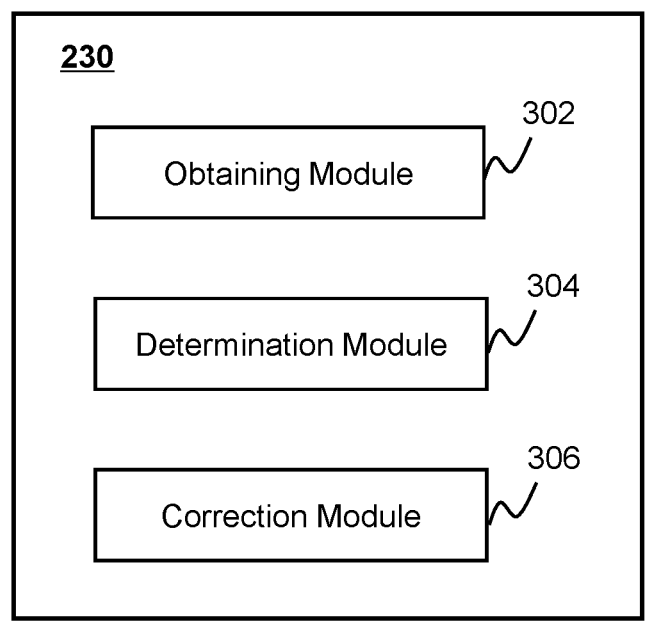
FIG. 3 is a block diagram illustrating an exemplary processing device according to some embodiments of the present disclosure.

FIG. 3 is a block diagram illustrating an exemplary processing device 230 according to some embodiments of the present disclosure. In some embodiments, the processing device 230 may be in communication with a computer-readable storage medium (e.g., a storage device of the time correction device 200) and execute instructions stored in the computer-readable storage medium. The processing device 130 may include an obtaining module 302, a determination module 304, and a correction module 306.

The obtaining module 302 may be configured to obtain a receiving time of a valid signal and correction information for correcting the receiving time. The correction information may include an amplitude and a duration of a target portion of the valid signal. More descriptions regarding the obtaining of the receiving time of the valid signal and the correction information may be found elsewhere in the present disclosure. See, e.g., operation 402 and relevant descriptions thereof.

The determination module 304 may be configured to determine a correlation coefficient between the amplitude and the duration of the target portion of the valid signal. The correlation coefficient may indicate a correlation between the amplitude and the duration of the target portion. The determination module 304 may be further configured to determine a correction value based on the correlation coefficient. The correction value may indicate a difference between the receiving time of the valid signal and a true receiving time of the valid signal. More descriptions regarding the determination of the correlation coefficient and the correction value may be found elsewhere in the present disclosure. See, e.g., operations 404 and 406, and relevant descriptions thereof.

The correction module 306 may be configured to determine a corrected receiving time of the valid signal by correcting the receiving time of the valid signal based on the correction value. More descriptions regarding the determination of the corrected receiving time may be found elsewhere in the present disclosure. See, e.g., operation 408 and relevant descriptions thereof.

It should be noted that the above descriptions of the processing device 230 are provided for the purposes of illustration, and not intended to limit the scope of the present disclosure. For persons having ordinary skills in the art, various variations and modifications may be conducted under the guidance of the present disclosure. However, those variations and modifications do not depart the scope of the present disclosure. In some embodiments, the processing device 230 may include one or more other modules. For example, the processing device 230 may include a storage module to store data generated by the modules in the processing device 230. In some embodiments, any two of the modules may be combined as a single module, and any one of the modules may be divided into two or more units.

Figure 4:
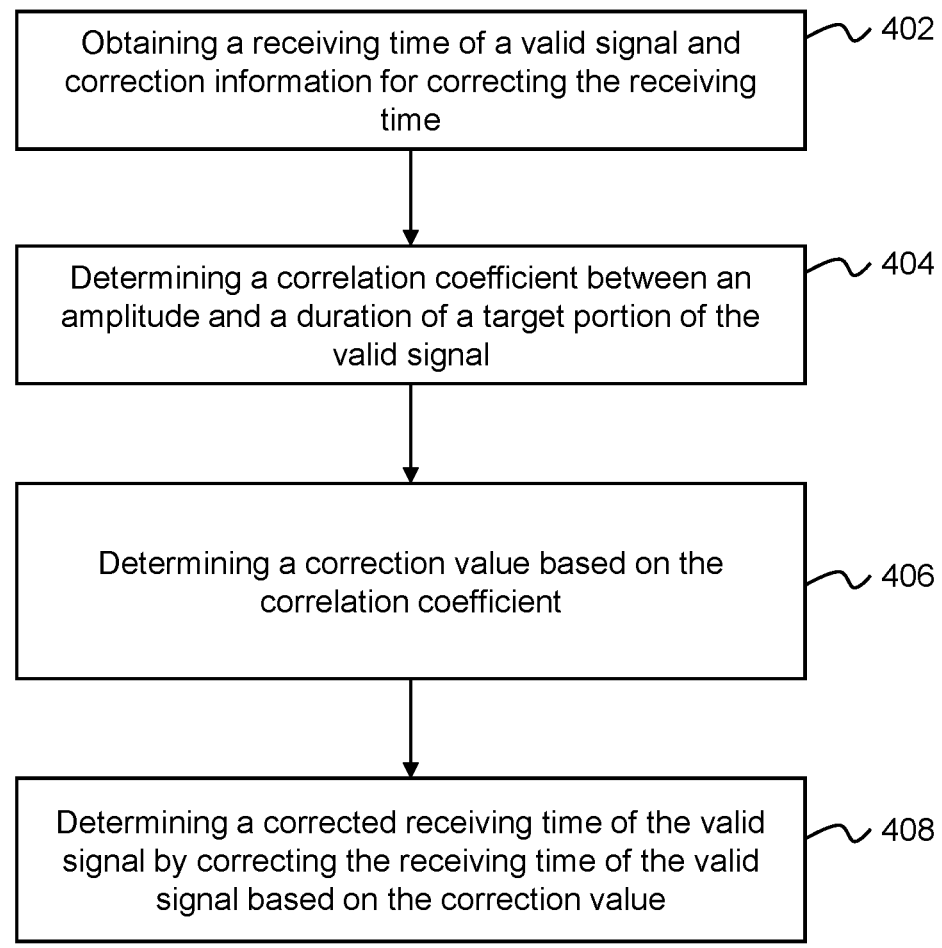
FIG. 4 is a flowchart illustrating an exemplary process for determining a corrected receiving time of a valid signal according to some embodiments of the present disclosure.

FIG. 4 is a flowchart illustrating an exemplary process for determining a corrected receiving time of a valid signal according to some embodiments of the present disclosure. Process 400 may be implemented in the time correction device 100 illustrated in FIG. 1 or the time correction device 200 illustrated in FIG. 2A. For example, the process 400 may be stored in a storage device in the form of instructions (e.g., an application), and invoked and/or executed by a processing device 230 (e.g., the processing device 230 illustrated in FIG. 2A, or one or more modules in the processing device 230 illustrated in FIG. 3). The operations of the illustrated process presented below are intended to be illustrative. In some embodiments, the process 400 may be accomplished with one or more additional operations not described, and/or without one or more of the operations discussed. Additionally, the order in which the operations of the process 400 as illustrated in FIG. 4 and described below is not intended to be limiting.

As aforementioned, a valid signal may include sub-signals with different amplitudes, or even if the valid signal includes only one signal or a same type of signal, an amplitude of the signal may fluctuate. During the transmission of the valid signal, a leading edge with a large amplitude may first reach the LED, and a leading edge with a small amplitude may reach the LED later than the leading edge with the large amplitude. That is, a correlation may exist between the amplitude and the receiving time of the valid signal. For instance, the larger the amplitude of the valid signal is, the quicker the valid signal reaches a timing threshold. That is, a signal slew rate of the valid signal may be positively correlated to the amplitude of the valid signal. Therefore, a measured receiving time of a valid signal with large amplitude may be earlier than a true receiving time of the valid signal, and a measured receiving time of a valid signal with small amplitude may be later than a true receiving time of the valid signal, which results in an inaccuracy in the receiving time determination.

According to some embodiments of the present disclosure, after the valid signal is received, the time correction device 200 may be configured to correct the receiving time of the valid signal. Specifically, the processing device 230 of the time correction device 200 may perform the process 400 to correct the receiving time of the valid signal.

In 402, the processing device 230 (e.g., the obtaining module 302) may obtain a receiving time of the valid signal and correction information for correcting the receiving time.

The correction information may include an amplitude and a duration of a target portion of the valid signal. Merely by way of example, the target portion may be a leading edge of the valid signal. In some embodiments, the processing device 230 may obtain the receiving time of the valid signal from the first time measurement component 210 or a storage device that stores the receiving time. In some embodiments, the processing device 230 may obtain the amplitude and the duration directly from the correction component 220 or a storage device that stores the amplitude and the duration.

In 404, the processing device 230 (e.g., the determination module 304) may determine a correlation coefficient between the amplitude and the duration of the target portion of the valid signal.

The correlation coefficient may indicate a correlation between the amplitude and the duration of the target portion. In some embodiments, the correlation coefficient determined based on the amplitude and the duration of the target portion of the valid signal may characterize a delay feature of the valid signal. In some embodiments, for different valid signals, the amplitudes and the durations of the target portions of the valid signals may be different, and the correlation coefficients of the different valid signals may be different.

In some embodiments, the correlation coefficient may represent a slew rate of the valid signal. For example, the correlation coefficient may be a ratio of the amplitude and the duration of the target portion of the valid signal.

In some embodiments, the processing device 230 may determine the correlation coefficient based on an algorithm. Exemplary algorithms may include a data fitting algorithm (e.g., a linear fitting algorithm, a polynomial fitting algorithm, an exponential fitting algorithm, a Gaussian fitting algorithm, a least square algorithm, etc.), a machine learning model-based algorithm (e.g., a neural network model, a statistical machine learning model, etc.), or the like, or any combination thereof. In some embodiments, a trained model may be obtained by training a preliminary model using a plurality of training samples. Each training sample may include a historical amplitude and a historical duration of a target portion of a sample valid signal, and a corresponding correlation coefficient of the sample valid signal. The processing device 230 may input the amplitude and the duration of the target portion of the valid signal into the trained model, and the trained model may output the correlation coefficient corresponding to the valid signal.

In some embodiments, the processing device 230 may determine the correlation coefficient based on a first corresponding relationship between the correlation coefficient, the amplitude of the target portion, and the duration of the target portion. The first corresponding relationship may be denoted in a table, a diagram, a mathematic function, etc., established based on historical amplitudes and historical durations of a plurality of historical valid signals and their respective correlation coefficients. For example, the first corresponding relationship may be denoted in a table including a plurality of rows, each of the rows may record an amplitude of a target portion of a historical valid signal, a duration of the target portion of the historical valid signal, and a reference value of the correlation coefficient corresponding to the historical valid signal. The processing device 230 may retrieve the corresponding correlation coefficient of the valid signal by looking up the table based on the amplitude and the duration of the valid signal. As another example, the first corresponding relationship may be represented by a curve plotted based on the amplitude and the duration of target portions of historical valid signals. The processing device 130 may determine a corresponding point of the valid signal from the curve based on the amplitude and the duration of the valid signal, and determine a slope of the point, wherein the slope is proportional to the correlation coefficient. Further, the processing device 230 may determine the correlation coefficient based on the slope.

In some embodiments, the processing device 230 may determine the correlation coefficient based on a mathematic function. The mathematic function may be a fitting function of the correlation coefficient determined based on historical amplitudes and historical durations of target portions of a plurality of historical valid signals. For example, the processing device 230 may determine the correlation coefficient by inputting the amplitude and the duration of the target portion of the valid signal into the mathematic function.

In 406, the processing device 230 may (e.g., the determination module 304) may determine a correction value based on the correlation coefficient.

The correction value may indicate a difference between the receiving time of the valid signal and a true receiving time of the valid signal. For example, the correction value may be a difference value between the receiving time of the valid signal and the true receiving time of the valid signal. As another example, the correction value may be a difference ratio of the true receiving time of the valid signal and the receiving time of the valid signal.

In some embodiments, the processing device 230 may designate the correlation coefficient as the correction value. That is, the correlation coefficient may be the same as the correction value. Therefore, a subsequent conversion may be avoided, and no additional component may be added, thereby improving an efficiency of the time correction.

In some embodiments, the processing device 230 may further process the correlation coefficient before designating the correlation coefficient as the correction value. For example, if the correction value is a difference ratio, the processing device 230 may convert the difference ratio to a difference value for subsequent processing. As another example, the processing device 230 may check the correlation coefficient based on the receiving time of the valid signal, so as to improve the accuracy and the reliability of time correction.

In 408, the processing device 230 may (e.g., the correction module 306) may determine the corrected receiving time of the valid signal by correcting the receiving time of the valid signal based on the correction value.

For example, if the correction value is a difference value, the corrected receiving time of the valid signal may be a sum value of the receiving time of the valid signal and the correction value. As another example, if the correction value is a difference ratio, the corrected receiving time of the valid signal may be a product of the difference ratio and the receiving time of the valid signal.

Some embodiments of the present disclosure provide a time correction device that corrects the receiving time of the valid signal based on the amplitude and the duration of the target portion of the valid signal, without performing an attenuate operation or a delay operation on the receiving time of the valid signal during the time correction. In this way, a time walk effect may be reduced or eliminated, which, in turn, improves the accuracy of the measurement of the receiving time of the valid signal.

It should be noted that the description of the process 400 is provided for the purposes of illustration, and not intended to limit the scope of the present disclosure. For persons having ordinary skills in the art, various variations and modifications may be conducted under the teaching of the present disclosure. For example, operations 402 and 404 may be integrated into a single operation. As another example, an additional operation for displaying the corrected receiving time may be added after operation 408. As still another example, the amplitude of the target portion in the above descriptions of FIGS. 2A to 4 may be replaced by an energy of the target portion. For example, the energy of the target portion of the valid signal may be measured, and further the correlation coefficient between the energy and the duration of the target portion of the valid signal may be determined. However, those variations and modifications may not depart from the protection of the present disclosure.

Figure 5:
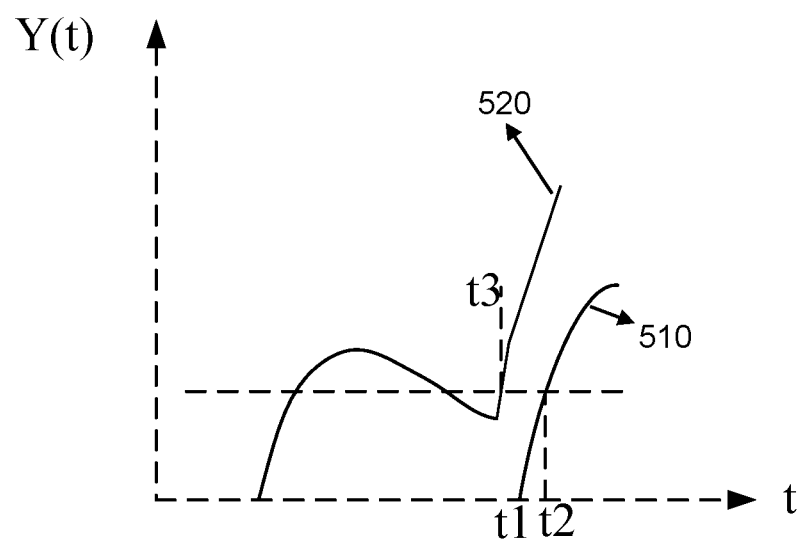
FIG. 5 is a schematic diagram illustrating a plurality of signals according to some embodiments of the present disclosure.

FIG. 5 is a schematic diagram illustrating a plurality of signals according to some embodiments of the present disclosure.

During signal transmission, an interference signal may be transmitted with a valid signal. For example, the interference signal may be superposed on the valid signal. The interference signal may be caused by various factors. An interference signal generated during PET imaging is taken as an example for illustration.

As aforementioned, in PET imaging, a receiving time of a gamma photon produced by a positron-electron annihilation event needs to be determined, and the accuracy of the determined receiving time may affect the determination accuracy of the position of the positron-electron annihilation event. A PET scanner may include a plurality of detectors (e.g., gamma ray detectors). The detector may include a scintillation crystal and a photovoltaic conversion component. The scintillation crystal may receive gamma photons. After the scintillation crystal receives the gamma photons, a weak light signal of the gamma photons may be converted, through the photovoltaic conversion component, into an electrical signal that a readout circuit can process. Normally, the count (or number) of photons converted into the electrical signal may be only hundreds to thousands. The limited count (or number) of photons may result in that a signal-to-noise ratio of the converted electrical signals is low. Therefore, an amplifier may be disposed in the PET scanner. The amplifier may be configured to amplify the electrical signals. A processor of the PET scanner may determine the receiving times of the gamma photons based on the amplified electrical signal.

During the above process, an interference signal may randomly appear in the gamma ray detector. The interference signal may include, for example, a dark count/noise, an optical crosstalk, and/or afterpulsing. The dark noise refers to a random avalanche discharge generated by a micro-unit due to thermal excitation in the absence of photon incident. The dark noise may be regarded as an interference superposed on the valid signal due to thermal excitation. The optical crosstalk may be generated because photons are generated in a Geiger avalanche, and the photons can irradiate into a surrounding micro-unit and trigger an avalanche. The afterpulsing may be generated because a carrier is temporarily captured during an avalanche, and then a new avalanche may be triggered when the carrier is released in a subsequent period.

Different crystals and detectors may undergo different interference signals. Therefore, it is desirable to provide devices and methods for time correction, which can efficiently reduce an effect of an interference signal, and increase the accuracy of the measurement of the receiving time of the valid signal.

FIG. 5 illustrates an exemplary valid signal 510 and a superposed signal 520 according to some embodiments of the present disclosure. The superposed signal 520 may be a superposition of the valid signal 510 and an interference signal (e.g., a dark noise, an optical crosstalk, etc.). A horizontal dotted line in FIG. 5 may indicate a base line. As shown in FIG. 5, a receiving time of the true valid signal 510 may be moment t3, and a receiving time of the superposed signal 520 may be indicated as moment t2.

According to FIG. 5, the moment t3 is earlier than the moment t2. That is, the receiving time of the superposed signal 520 is earlier than the reception time of the valid signal 510. Therefore, if the receiving time of the valid signal 520 is measured by measuring the receiving time of the superposed signal 520, the receiving time of the valid signal 520 may be inaccurate because of the interference signal.

Figure 6A:
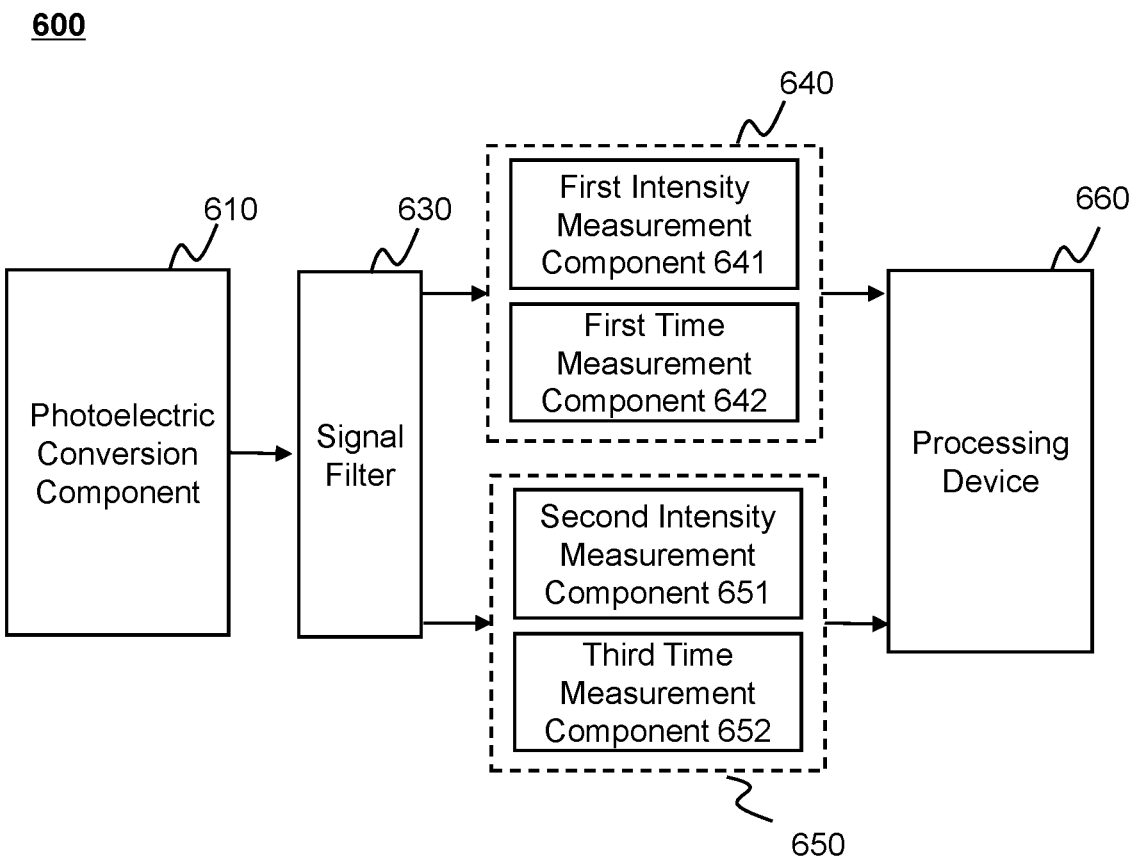
FIG. 6A is a schematic diagram illustrating an exemplary time correction device according to some embodiments of the present disclosure.

FIG. 6A is a schematic diagram illustrating an exemplary time correction device 600 according to some embodiments of the present disclosure. The time correction device 600 may be an embodiment of the time correction device 100 as described in FIG. 1.

Since an interference signal (e.g., a dark count/noise, an optical crosstalk, etc.) is difficult to remove, and occurs randomly, in order to reduce or eliminate the effect of the interference signal, and improve a measurement accuracy of a receiving time of a valid signal, the time correction device 600 may be provided. As shown in FIG. 6A, the time correction device 600 may include a photoelectric conversion component 610, a signal filter 630, a first measurement component 640, a second measurement component 650, and a processing device 660.

The photoelectric conversion component 610 may be configured to receive an excitation signal and convert the excitation signal into an input signal. The photoelectric conversion component 610 may be similar to the photoelectric conversion component 250 as described in FIG. 2D, which is not be repeated herein. In some embodiments, during the receiving process and/or the conversion process, an interference signal (e.g., a dark noise, an optical crosstalk, afterpulsing, etc.) may be generated and superposed on a valid signal. The input signal may be a superposition of the valid signal and the interference signal. If the input signal is used for timing, the receiving time of the valid signal may be inaccurate, thereby deteriorating time resolution. Therefore, the input signal may need to be processed (e.g., filtered), which reduces or eliminates the effect that a shift of a base line corresponding to the valid signal is caused by the superposition.

In some embodiments, the signal filter 630 may generate a filtered input signal by performing a filtering operation on the input signal. For example, the signal filter 630 may process the input signal using a filtering algorithm to obtain the filtered input signal. Exemplary filtering algorithms may include a Wiener filtering algorithm, a Kalman filtering algorithm, a matching filtering algorithm, a wavelet filtering algorithm, an adaptive filtering algorithm, an average filtering algorithm, a Gaussian filtering algorithm, a convolution filtering algorithm, a filtering algorithm based on support vector machine, or the like, or any combination thereof.

In some embodiments, the signal filter 630 may further extract a first portion of the filtered input signal as the interference signal. An amplitude of the first portion may be larger than a first threshold and smaller than a second threshold. The signal filter 630 may also extract a second portion of the filtered input signal as the valid signal. An amplitude of the second portion may be larger than the second threshold. In some embodiments, the first threshold may be similar to the timing threshold, and the second threshold may be similar to the amplitude threshold as described in connection with FIG. 1. In some embodiments, the second threshold may be greater than the first threshold.

Figure 10A:
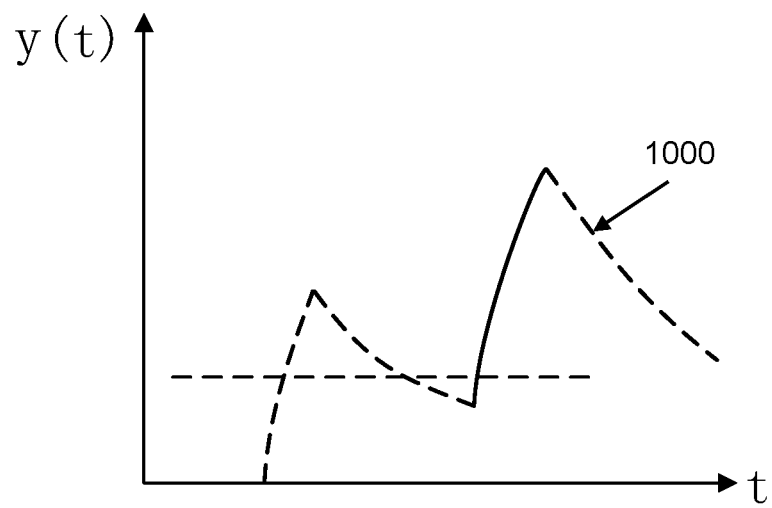
FIG. 10A is a schematic diagram illustrating an exemplary input signal according to some embodiments of the present disclosure.
Figure 10B:
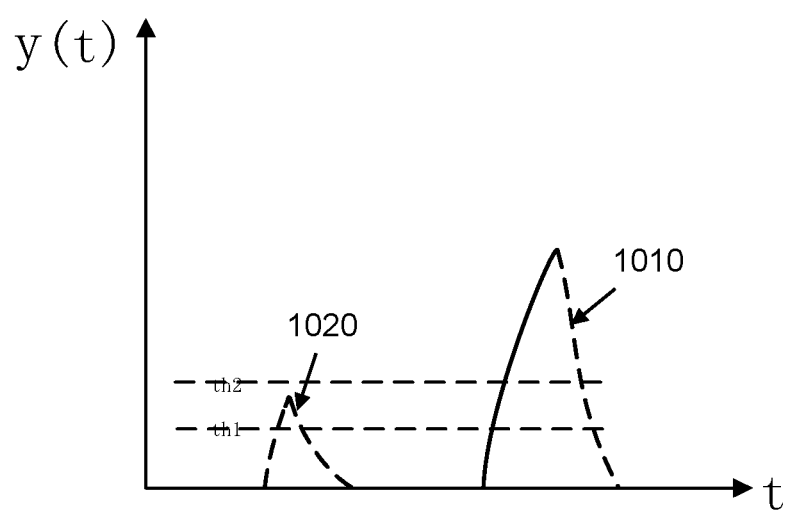
FIG. 10B is a schematic diagram illustrating a valid signal and an interference signal according to some embodiments of the present disclosure.

For illustration purposes, FIG. 10A and FIG. 10B are provided. FIG. 10A is a schematic diagram illustrating an exemplary input signal 1000 according to some embodiments of the present disclosure. FIG. 10B is a schematic diagram illustrating a valid signal 1010 and an interference signal 1020 according to some embodiments of the present disclosure. As shown in FIG. 10A and FIG. 10B, the input signal 1000 is a superposition of the valid signal 1010 and the interference signal 1020. A signal filter (e.g., the signal filter 630) may perform the filtering operation on the input signal 1000 so as to obtain the interference signal 1010 and the valid signal 1020. As used herein, the amplitude of the interference signal 1010 may be larger than the first threshold ("th1" in FIG. 10B) and smaller than the second threshold ("th2" in FIG. 10B), and the amplitude of the valid signal 1010 may be larger than the second threshold.

In some embodiments, the signal filter 630 may include an analog filter, a digital filter, or a combination thereof. Exemplary analog filters may include a passive filter, an active filter, etc. Exemplary digital filters may include a shaping filter, a Butterworth filter, a Chebyshev filter, an Elliptic filter, a Bessel filter, a finite impulse response (FIR) filter, or the like, or any combination thereof. Merely by way of example, the signal filter 630 may be a shaping filter, which may reduce a width of the interference signal (e.g., a dark noise) and a width of the valid signal, thereby reducing a probability that the interference signal is superposed on the valid signal. Therefore, the interference signal and the valid signal may be distinguished, thereby reducing an effect of the interference signal on the valid signal, which, in turn, improves an accuracy of the measurement of the receiving time of the valid signal and the time resolution.

In some embodiments, the signal filter 630 may be connected to the first measurement component 640 and the second measurement component 650. For example, an output terminal of the signal filter 630 may be connected to an input terminal of the first measurement component 640 and an input terminal of the second measurement component 650. As another example, the signal filter 630 may include a first output terminal and a second output terminal. The first output terminal of the signal filter 630 may be connected to an input terminal of the first measurement component 640, and the second output terminal of the signal filter 630 may be connected to an input terminal of the second measurement component 650. In some embodiments, the signal filter 630 may transmit the valid signal and the interference signal to the first measurement component 640 and the second measurement component 650, respectively.

The first measurement component 640 may be configured to measure the receiving time of the valid signal and the intensity of the valid signal. In some embodiments, the first measurement component 640 may include a first intensity measurement component 641 and a first time measurement component 642. The first intensity measurement component 641 may be configured to measure the intensity of the valid signal. The intensity of the valid signal may be used for image reconstruction. In some embodiments, the intensity of the valid signal may include an amplitude and/or an energy of the valid signal. Correspondingly, the first intensity measurement component 641 may include an amplitude measurement component and/or an energy measurement component. The amplitude measurement component may be similar to the amplitude measurement component 221 as described in FIG. 2B. Exemplary energy measurement components may include an energy detector, an energy sensor, or the like, or any combination thereof. In some embodiments, the energy of the valid signal may be obtained by integrating the amplitude of the valid signal. The first time measurement component 642 may be configured to measure the receiving time of the valid signal. In some embodiments, the first time measurement component 642 may include a timer, a time meter, a chronoscope, a calculagraph, a leading edge discriminator (LED), or the like, or any combination thereof. In some embodiments, the first time measurement component 642 may be an embodiment of the time measurement component 110 as described in connection with FIG. 1.

The second measurement component 650 may be configured to measure the receiving time of the interference signal and the intensity of the interference signal. In some embodiments, the second measurement component 650 may include a second intensity measurement component 651 and a third time measurement component 652. The second intensity measurement component 651 may be configured to measure the intensity of the interference signal. The second intensity measurement component 651 may be similar to the first intensity measurement component 641. The third time measurement component 652 may be configured to measure the receiving time of the interference signal. The third time measurement component 652 may be similar to the first time measurement component 642.

In some embodiments, the first intensity measurement component 641 may be further configured to measure an amplitude of a target portion of the valid signal, and the first time measurement component 642 may be further configured to measure a duration of the target portion of the valid signal. Additionally or alternatively, the second intensity measurement component 651 may be further configured to measure an amplitude of a target portion of the interference signal, and the third time measurement component 652 may be further configured to measure a duration of the target portion of the interference signal. A corrected receiving time of the valid signal may be obtained by correcting the receiving time of the valid signal based on the amplitude of the target portion of the valid signal and the duration of the target portion of the valid signal (e.g., by performing the process 400 as shown in FIG. 4), and a corrected receiving time of the interference signal may be obtained by correcting the receiving time of the interference signal based on the amplitude of the target portion of the interference signal and the duration of the target portion of the interference signal (e.g., by performing the process 400 as shown in FIG. 4). Therefore, a time walk effect may be reduced or eliminated in measuring the receiving time of the valid signal.

The processing device 660 may be configured to determine a corrected receiving time of the valid signal by correcting the receiving time of the valid signal based on correction information. In some embodiments, the correction information may be collected by, for example, the second intensity measurement component 651, the third time measurement component 652, etc. For example, the correction information may include the receiving time of the interference signal collected by the third time measurement component 652 and/or the intensity of the interference signal collected by the second intensity measurement component 651. More descriptions of the determination of the corrected receiving time based on the receiving time and/or intensity of the interference signal may be found elsewhere in the present disclosure (e.g., FIG. 8 and FIGS. 9A-9B, and the descriptions thereof).

In some embodiments, the processing device 660 may be connected to the first measurement component 640 and the second measurement component 650. For example, an input terminal of the processing device 660 may be electrically connected to an output terminal of the first measurement component 640 and an output terminal of the second measurement component 650, respectively. As another example, the processing device 660 may include a first input terminal and a second input terminal. The first input terminal of the processing device 660 may be electrically connected to an output terminal of the first measurement component 640, and the second input terminal of the processing device 660 may be electrically connected to an output terminal of the second measurement component 650. In some embodiments, the processing device 660 may be an embodiment of the processing device 130 as described in connection with FIG. 1.

It should be noted that the time correction device 600 is provided for illustration purposes, and not intended to limit the scope of the present disclosure. For persons having ordinary skills in the art, multiple variations and modifications may be made under the teachings of the present disclosure. However, those variations and modifications do not depart from the scope of the present disclosure. For example, the time correction device 600 may further include a storage device configured to store data and/or instructions used for time correction. As another example, the first intensity measurement component 641 and/or the second intensity measurement component 651 may be omitted. For instance, the time correction device 600 may measure an annihilate time of the valid signal, and determine the intensity of the valid signal based on the receiving time of the valid signal and the annihilate time of the valid signal. As another example, the time correction device 600 may measure an annihilate time of the interference signal, and determine the intensity of the interference signal based on the receiving time of the interference signal and the annihilate time of the interference signal. As still another example, the time correction device 600 may measure an annihilate time of the interference signal and an amplitude of the interference signal, and determine an energy of the interference signal by integrating the amplitude of the interference signal based on the receiving time of the interference signal and the annihilate time of the interference signal.

Figure 6B:
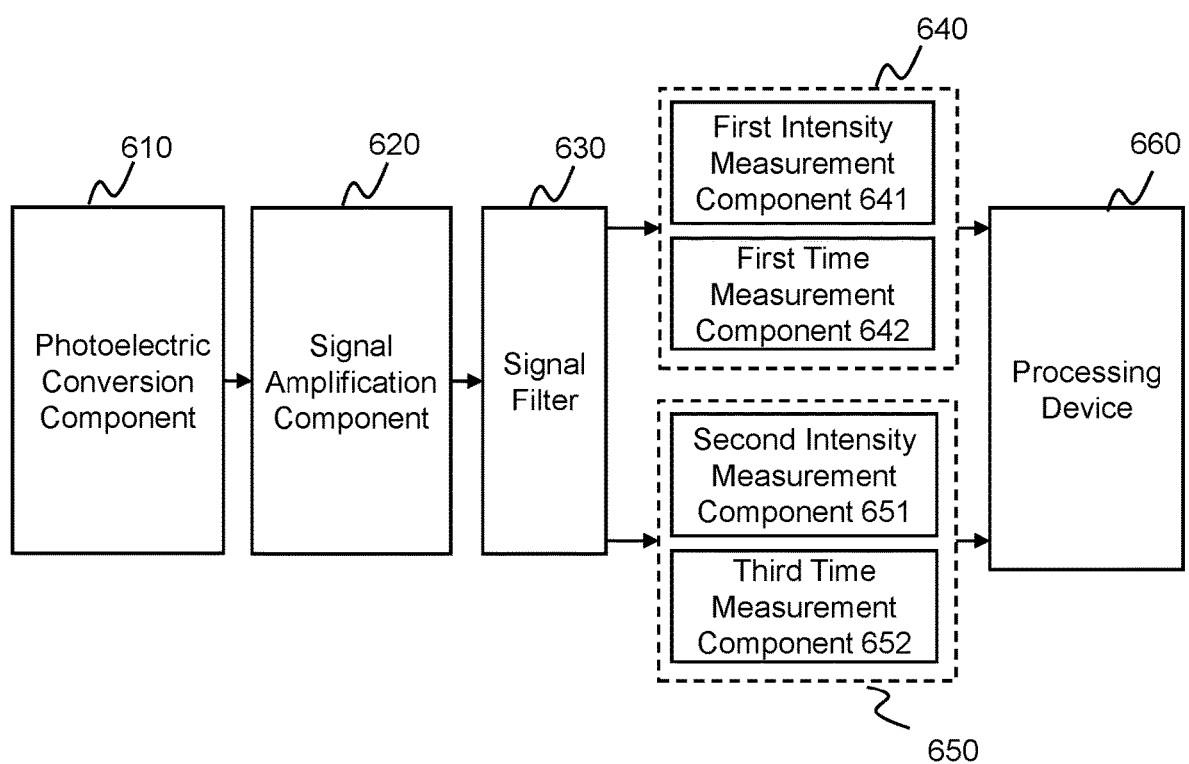
FIG. 6B is a schematic diagram illustrating another exemplary time correction device according to some embodiments of the present disclosure.

In some embodiments, the time correction device 600 may further include a signal amplification component 620 as shown in FIG. 6B. The signal amplification component 620 may receive the input signal from the photoelectric conversion component 610. The signal amplification component 620 may generate an amplified input signal by amplifying the input signal and transmit the amplified input signal to the signal filter 630. The signal filter 630 may be configured to obtain the valid signal and the interference signal by filtering the amplified input signal. In some embodiments, the signal amplification component 620 may be connected to the photoelectric conversion component 610 and the signal filter 630, respectively. For example, an output terminal of the photoelectric conversion component 610 may be connected to an input terminal of the signal amplification component 620, and an output terminal of the signal amplification component 620 may be connected to an input terminal of the signal filter 630. In some embodiments, the signal amplification component 620 may be similar to the signal amplification component 240 as described in connection with FIG. 2D. In some embodiments, during the amplification of the input signal, a timing error may be generated. By collecting the correction information for correcting the receiving time of the valid signal (i.e., the receiving time and/or the intensity of the interference signal), the processing device 660 may further reduce or eliminate the timing error.

In some embodiments, the time correction device 600 may be applied to other scenarios, such as, a photoelectric detection system, a wireless detection system, etc., for reducing or eliminating the effect of the interference signal and/or improving an accuracy of timing. In addition, the time correction device 600 may be further used to reduce or eliminate an effect of the interference signal on intensity linearity.

Figure 7:
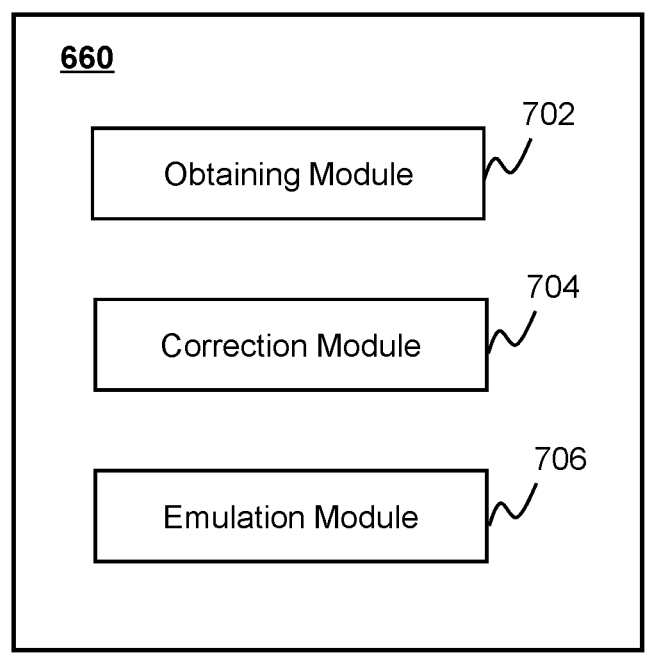
FIG. 7 is a block diagram illustrating an exemplary processing device according to some embodiments of the present disclosure.

FIG. 7 is a block diagram illustrating an exemplary processing device 660 according to some embodiments of the present disclosure. In some embodiments, the processing device 660 may be in communication with a computer-readable storage medium (e.g., a storage device of the time correction device 600) and may execute instructions stored in the computer-readable storage medium. The processing device 660 may include an obtaining module 702, a correction module 704, and an emulation module 706.

The obtaining module 702 may be configured to obtain a receiving time of a valid signal and correction information for correcting the receiving time of the valid signal, wherein the correction information may include a receiving time and/or an intensity of the interference signal. More descriptions regarding the obtaining of the receiving time of the valid signal and the correction information may be found elsewhere in the present disclosure. See, e.g., operation 802 and relevant descriptions thereof.

The correction module 704 may be configured to determine a corrected receiving time of the valid signal by correcting the receiving time of the valid signal based on the correction value. More descriptions regarding the determination of the corrected receiving time may be found elsewhere in the present disclosure. See, e.g., operation 804 and relevant descriptions thereof.

The emulation module 706 may be configured to determine a corresponding relationship (e.g., a second corresponding relationship, a third corresponding relationship, and/or a fourth corresponding relationship). More descriptions regarding the determination of the corrected receiving time may be found elsewhere in the present disclosure. See, e.g., FIGS. 9A-9B, and relevant descriptions thereof.

It should be noted that the above descriptions of the processing device 660 are provided for the purposes of illustration, and not intended to limit the scope of the present disclosure. For persons having ordinary skills in the art, various variations and modifications may be conducted under the guidance of the present disclosure. However, those variations and modifications do not depart the scope of the present disclosure. In some embodiments, the processing device 660 may include one or more other modules. For example, the processing device 660 may include a storage module to store data generated by the modules in the processing device 660. In some embodiments, any two of the modules may be combined as a single module, and any one of the modules may be divided into two or more units.

Figure 8:
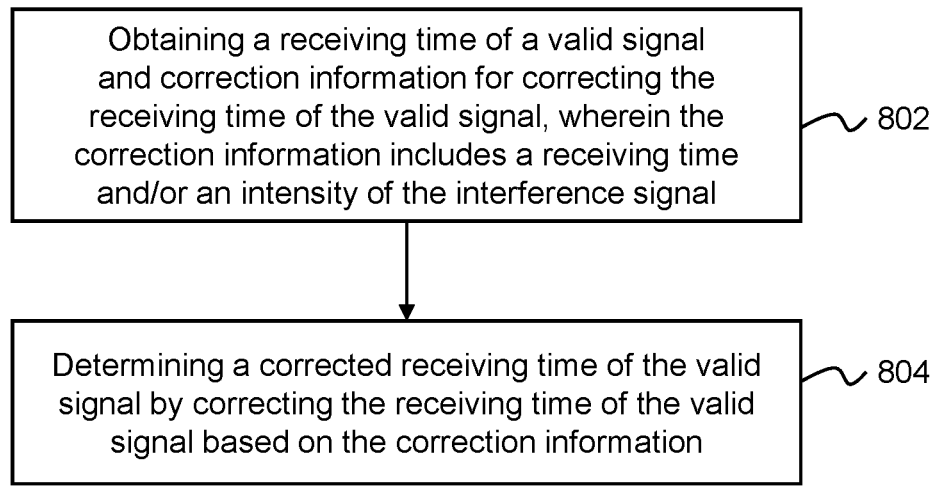
FIG. 8 is a flowchart illustrating an exemplary process for determining a corrected receiving time of a valid signal according to some embodiments of the present disclosure.

FIG. 8 is a flowchart illustrating an exemplary process for determining a corrected receiving time of a valid signal according to some embodiments of the present disclosure. Process 800 may be implemented in the time correction device 100 illustrated in FIG. 1 or the time correction device 600 illustrated in FIGS. 6A-6B. For example, the process 800 may be stored in a storage device in the form of instructions (e.g., an application), and invoked and/or executed by the processing device 660 (e.g., the processing device 660 illustrated in FIGS. 6A-6B, or one or more modules in the processing device 660 illustrated in FIG. 7). The operations of the illustrated process presented below are intended to be illustrative. In some embodiments, the process 800 may be accomplished with one or more additional operations not described, and/or without one or more of the operations discussed. Additionally, the order in which the operations of the process 800 as illustrated in FIG. 8 and described below is not intended to be limiting.

Since an interference signal (e.g., a dark count/noise, an optical crosstalk, etc.) is difficult to remove, and occurs randomly, in order to reduce or eliminate an effect of the interference signal, and improve an accuracy of a receiving time of a valid signal, the process 800 may be provided.

In 802, the processing device 660 (e.g., the obtaining module 702) may obtain a receiving time of a valid signal and correction information for correcting the receiving time of the valid signal, wherein the correction information may include a receiving time and/or an intensity of the interference signal.

In some embodiments, the processing device 660 may obtain the receiving time of the valid signal from the first time measurement component 642 or a storage device that stores the receiving time of the valid signal. The processing device 660 may obtain the receiving time of the interference signal from the third time measurement component 652 or a storage device that stores the receiving time of the interference signal. The processing device 660 may obtain the intensity of the interference signal from the second intensity measurement component 651 or a storage device that stores the intensity of the interference signal.

In some embodiments, the processing device 660 may obtain the receiving time of the interference signal and an annihilate time of the interference signal, and determine the intensity of the interference signal based on the receiving time of the interference signal and the annihilate time of the interference signal. For example, the processing device 660 may determine the intensity of the interference signal using a fitting algorithm (e.g., a polynomial fitting algorithm, a least square algorithm, etc.).

In 804, the processing device 660 (e.g., the correction module 704) may determine a corrected receiving time of the valid signal by correcting the receiving time of the valid signal based on the correction information.

In some embodiments, if the correction information includes the receiving time of the interference signal, the processing device 660 may determine a receiving time difference between the valid signal and the interference signal by comparing the receiving time of the interference signal and the receiving time of the valid signal. The receiving time difference may indicate a degree of interference of the interference signal on the valid signal. The receiving time difference may include a positive value or a negative value. If the receiving time of the interference signal is close to the receiving time of the valid signal, the receiving time difference may be small, and the degree of interference of the interference signal on the valid signal may be large. If the receiving time of the interference signal is far away from the receiving time of the valid signal, the receiving time difference may be large, and the degree of interference of the interference signal on the valid signal may be small.

In some embodiments, the processing device 660 may correct the receiving time of the valid signal based on the receiving time difference. Since the receiving time difference indicates the degree of interference of the interference signal on the valid signal, a correction value may be determined based on the receiving time difference. For instance, the correction value may have a negative correlation with the receiving time difference (i.e., the smaller the receiving time difference, the larger the correction value). Further, the processing device 660 may determine the corrected receiving time based on the correction value. For example, the processing device 660 may obtain a product of the correlation value and the receiving time of the valid signal, and designate the product as the corrected receiving time of the valid signal. As another example, the processing device 660 may determine a sum of the correction value and the receiving time of the valid signal, and designate the sum as the corrected receiving time of the valid signal.

In some embodiments, the processing device 660 may obtain a second corresponding relationship between correction values and receiving time differences between the valid signal and the interference signal. The second corresponding relationship may include at least one pair of a reference value of the receiving time difference (or referred to as an emulation receiving time difference) and a corresponding reference value of the correction value (or referred to as an emulation correction value). The second corresponding relationship may be represented as a table, a diagram, a model, a mathematic function, or the like, or any combination thereof. In some embodiments, the second corresponding relationship may be determined based on experience of a user (e.g., a technician, a doctor, a physicist, etc.). In some embodiments, the second corresponding relationship may be determined based on statistical results of a plurality of sets of historical data, wherein each set of the historical data may include a receiving time of a historical valid signal, a receiving time of a historical interference signal, a receiving time of a historical input signal (i.e., the valid signal with the interference signal). The historical data may be obtained by any measurement manner.

Alternatively, the second corresponding relationship may be determined based on a plurality of emulation interference signals and a plurality of emulation valid signals. More descriptions of the determination of the second corresponding relationship may be found elsewhere in the present disclosure (e.g., FIG. 9A and the descriptions thereof). The processing device 660 may determine the correction value based on the receiving time difference and the second corresponding relationship. For example, if the second corresponding relationship is a table, the processing device 660 may determine the correction value by retrieving the second corresponding relationship by looking up the table based on the receiving time difference. As another example, if the second corresponding relationship is a model, the processing device 660 may input the receiving time difference as an input, and determine an output of the model as the correction value.

In some embodiments, if the correction information includes the intensity of the interference signal, the processing device 660 may correct the receiving time of the valid signal based on the intensity of the interference signal. The intensity of the interference signal may indicate a degree of interference of the interference signal on the valid signal. If the intensity of the interference signal is large, the degree of interference of the interference signal on the valid signal may be large. If the intensity of the interference signal is small, the degree of interference of the interference signal on the valid signal may be small.

Since the intensity of the interference signal indicates the degree of interference of the interference signal on the valid signal, a correction value may be determined based on the intensity of the interference signal. For instance, the correction value may have a positive correlation with the intensity of the interference signal (i.e., the larger the intensity of the interference signal, the larger the correction value). Further, the processing device 660 may determine the corrected receiving time based on the correction value. For example, the processing device 660 may obtain a product of the correlation value and the receiving time of the valid signal, and designate the product as the corrected receiving time of the valid signal. As another example, the processing device 660 may determine a sum of the correction value and the receiving time of the valid signal, and designate the sum as the corrected receiving time of the valid signal.

In some embodiments, the processing device 660 may obtain a third corresponding relationship between correction values and intensities of the interference signal. The third corresponding relationship may include at least one pair of a reference value of the intensity of the interference signal (or referred to as an emulation intensity of an emulation interference signal) and a corresponding reference value of the correction value (or referred to as an emulation correction value). The third corresponding relationship may include a table, a diagram, a model, a mathematic function, or the like, or any combination thereof. In some embodiments, the third corresponding relationship may be determined similar to the determination of the second corresponding relationship. More descriptions of the determination of the third corresponding relationship may be found elsewhere in the present disclosure (e.g., FIG. 9B and the descriptions thereof). The processing device 660 may determine the correction value based on the intensity of the interference signal and the third corresponding relationship, and determine the corrected receiving time of the valid signal by correcting the receiving time of the valid signal based on the correction value, which is similar to the determination of the correction value based on the receiving time difference.

In some embodiments, if the correction information includes the receiving time of the interference signal and the intensity of the interference signal, the processing device 660 may determine the receiving time difference between the valid signal and the interference signal. Since each of the receiving time difference and the intensity of the interference signal indicates the degree of interference of the interference signal on the valid signal, the processing device 660 may correct the receiving time of the valid signal based on both the receiving time difference and the intensity of the interference signal. For instance, the processing device 660 may determine a weight value of each of the receiving time difference and the intensity of the interference signal, determine a first correction value based on the receiving time difference (e.g., according to the second corresponding relationship), determine a second correction value based on the intensity of the interference signal (e.g., according to the third corresponding relationship). Further, the processing device 660 may correct the receiving time of the valid signal based on the first correction value, the second correction value, and the weight value of each of the receiving time difference and the intensity of the interference signal.

In some embodiments, the processing device 660 may obtain a fourth corresponding relationship between correction values, receiving time differences between the valid signal and the interference signal, and intensities of the interference signal. The fourth corresponding relationship may include at least one pair of a reference value of the receiving time difference (or referred to as an emulation receiving time difference), a reference value of the intensity of the interference signal (or referred to as an emulation intensity of an emulation interference signal), and a corresponding reference value of the correction value (or referred to as an emulation correction value). The fourth corresponding relationship may include a table, a diagram, a model, a mathematic function, or the like, or any combination thereof. In some embodiments, the fourth corresponding relationship may be determined similar to the determination of the second corresponding relationship or the third corresponding relationship. In some embodiments, the fourth corresponding relationship may be determined based on the second corresponding relationship and the third corresponding relationship. The processing device 660 may determine a correction value based on the receiving time difference, the intensity of the interference signal, and the fourth corresponding relationship, and determine the corrected receiving time of the valid signal by correcting the receiving time of the valid signal based on the correction value, which is similar to the determination of the correction value based on the receiving time difference.

According to some embodiments of the present disclosure, the input signal may be filtered to reduce the effect of the interference signal on the valid signal. In addition, the correction information (e.g., the receiving time of the interference signal and/or the intensity of the interference signal) may be collected, and the receiving time of the valid signal may be corrected based on the correction information, which reduces the effect of the interference signal on the valid signal, and improves the accuracy of the measurement of the receiving time of the valid signal. Besides, the process 800 may be easy to be performed, without greatly increasing a complexity of the measurement of the receiving time of the valid signal.

It should be noted that the description of the process 800 is provided for the purposes of illustration, and not intended to limit the scope of the present disclosure. For persons having ordinary skills in the art, various variations and modifications may be conducted under the teaching of the present disclosure. For example, operations 802 and 804 may be integrated into a single operation. As another example, an additional operation for image display may be added after operation 806. However, those variations and modifications may not depart from the protection of the present disclosure.

In some embodiments, the correction information may include an amplitude of a target portion of the valid signal, a duration of the target portion of the valid signal, an amplitude of a target portion of the interference signal, and a duration of the target portion of the interference signal. Therefore, before obtaining the receiving time difference between the valid signal and the interference signal, the receiving time of the valid signal and/or the receiving time of the interference signal may be corrected. For instance, the processing device 660 may obtain an initial corrected receiving time of the valid signal by correcting the receiving time of the valid signal based on the amplitude of the target portion of the valid signal and the duration of the target portion of the valid signal (e.g., by performing the process 400 as shown in FIG. 4). The processing device 660 may also obtain an initial corrected receiving time of the interference signal by correcting the receiving time of the interference signal based on the amplitude of the target portion of the interference signal and the duration of the target portion of the interference signal (e.g., by performing the process 400 as shown in FIG. 4). Further, the processing device 660 may obtain the receiving time difference between the valid signal and the interference signal based on the initial corrected receiving time of the valid signal and the initial corrected receiving time of the interference signal. Therefore, a time walk effect may be reduced or eliminated which further improves an accuracy of the measurement of the receiving time of the valid signal.

Figure 9A:
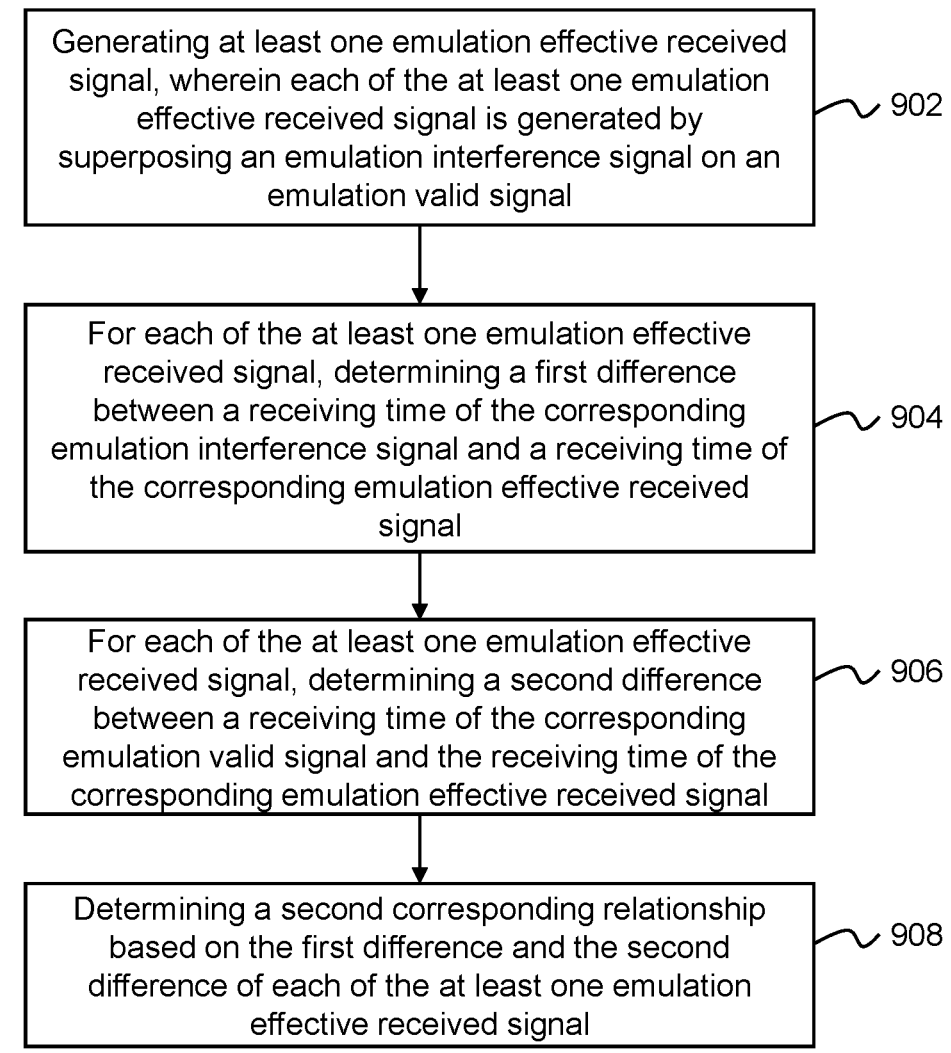
FIG. 9A is a flowchart illustrating an exemplary process for determining a second corresponding relationship between correction values and receiving time differences according to some embodiments of the present disclosure.

FIG. 9A is a flowchart illustrating an exemplary process for determining a second corresponding relationship between correction values and receiving time differences according to some embodiments of the present disclosure. In some embodiments, the process 900 may be performed to achieve at least part of operation 804 as described in connection with FIG. 8.

In 902, the processing device 660 (e.g., the emulation module 706) may generate at least one emulation effective received signal.

Each of the emulation effective received signal may be generated by superposing an emulation interference signal on an emulation valid signal. The emulation valid signal may be used to emulate a valid signal that has not been influenced by any interference signal, the emulation interference signal may be used to emulate an interference signal. An emulation effective received signal may be used to emulate a valid signal that has been influenced by an interference signal.

In some embodiments, the processing device 660 may obtain an emulation effective received signal using a signal emulator. The signal emulator may generate an emulation interference signal and an emulation valid signal, and generate the emulation effective received signal by superposing the emulation interference signal on the emulation valid signal. The signal emulator may include any devices or applications that can perform signal emulation. For example, the signal emulator may include a signal emulation software, for example, "sipm model," "Altium Designer," "Cadence," "TINA-TI," or the like, or any combination thereof. In some embodiments, the processing device 660 may obtain the emulation interference signal and the emulation valid signal based on historical signals received or generated in historical signal processing operations. For example, the processing device 660 may obtain a historical valid signal and a corresponding historical interference signal from a storage device, and designate the historical valid signal and the corresponding historical interference signal as the emulation interference signal and the emulation valid signal, respectively.

In 904, for each of the at least one emulation effective received signal, the processing device 660 (e.g., the emulation module 706) may determine a first difference between a receiving time of the corresponding emulation interference signal and a receiving time of the corresponding emulation effective received signal.

In some embodiments, the receiving time of the corresponding emulation interference signal and the receiving time of the corresponding emulation effective received signal may be determined by the processing device 660 by analyzing amplitude values of the emulation interference signal and the emulation effective received signal. Alternatively, the receiving time of the corresponding emulation interference signal and the receiving time of the corresponding emulation effective received signal may be determined by the signal emulator.

In 906, for each of the at least one emulation effective received signal, the processing device 660 (e.g., the emulation module 706) may determine a second difference between a receiving time of the corresponding emulation valid signal and the receiving time of the corresponding emulation effective received signal.

The receiving time of the corresponding emulation valid signal may be determined by the processing device 660 by analyzing amplitude values of the emulation valid signal. Alternatively, the receiving time of the corresponding emulation valid signal may be determined by the signal emulator.

In 908, the processing device 660 (e.g., the emulation module 706) may determine the second corresponding relationship between correction values and receiving time differences based on the first difference and the second difference of each of the at least one emulation effective received signal.

As described in connection with operation 804, the second corresponding relationship may include at least one pair of a reference value of the receiving time difference and a corresponding reference value of the correction value. For example, the first difference of a specific emulation effective received signal may be designated as a reference value of the receiving time difference, and the second difference of the specific emulation effective received signal may be designated as a corresponding reference value of the correction value.

In some embodiments, the processing device 660 may determine the second corresponding relationship, for example, using a mapping technique, a fitting technique, a machine learning technique, or the like, or any combination thereof.

Figure 9B:
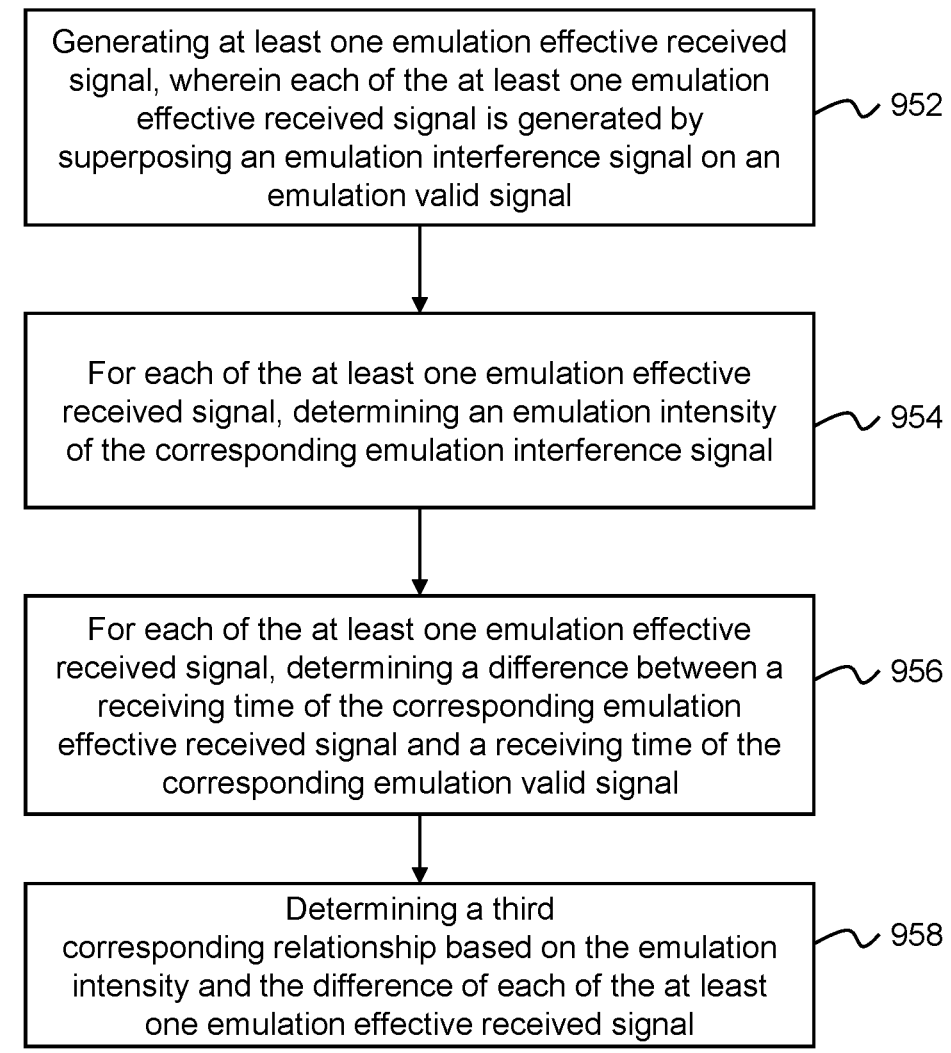
FIG. 9B is a flowchart illustrating an exemplary process for determining a third corresponding relationship between correction values and intensities of an interference signal according to some embodiments of the present disclosure.

FIG. 9B is a flowchart illustrating an exemplary process for determining a third corresponding relationship between correction values and intensities of an interference signal according to some embodiments of the present disclosure. In some embodiments, the process 950 may be performed to achieve at least part of operation 804 as described in connection with FIG. 8.

In 952, the processing device 660 (e.g., the emulation module 706) may generate at least one emulation effective received signal.

Each of the emulation effective received signal may be generated by superposing an emulation interference signal on an emulation valid signal. Operation 952 may be performed in a similar manner as operation 902, and the descriptions thereof are not repeated here.

In 954, for each of the at least one emulation effective received signal, the processing device 660 (e.g., the emulation module 706) may determine an emulation intensity of the corresponding emulation interference signal.

In some embodiments, the emulation intensity of the corresponding emulation interference signal may be determined by the processing device 660 by analyzing amplitude values of the emulation valid signal. Alternatively, the emulation intensity of the corresponding emulation valid signal may be determined by the signal emulator.

In 956, for each of the at least one emulation effective received signal, the processing device 660 (e.g., the emulation module 706) may determine a difference between a receiving time of the corresponding emulation valid signal and a receiving time of the corresponding emulation effective received signal.

The receiving time of the corresponding emulation valid signal and the receiving time of the corresponding emulation effective received signal may be determined by the processing device 660 by analyzing amplitude values of the emulation valid signal and the emulation effective received signal. Alternatively, the receiving time of the corresponding emulation valid signal and the receiving time of the corresponding emulation effective received signal may be determined by the signal emulator.

In 958, the processing device 660 (e.g., the emulation module 706) may determine the third corresponding relationship between correction values and intensities of the interference signal based on the emulation intensity and the difference of each of the at least one emulation effective received signal.

As described in connection with operation 804, the third corresponding relationship may include at least one pair of a reference value of the intensity of the interference signal and a corresponding reference value of the correction value. For example, the emulation intensity of a specific emulation effective received signal may be designated as a reference value of the intensity of the interference signal, and the difference of the specific emulation effective received signal may be designated as a corresponding reference value of the correction value.

In some embodiments, the processing device 660 may determine the third corresponding relationship, for example, using a mapping technique, a fitting technique, a machine learning technique, or the like, or any combination thereof.

It should be noted that the descriptions of the process 900 and the process 950 are provided for the purposes of illustration, and not intended to limit the scope of the present disclosure. For persons having ordinary skills in the art, various variations and modifications may be conducted under the teaching of the present disclosure. In some embodiments, the processing device 660 may further determine a fourth corresponding relationship between the receiving time differences between the valid signal and the interference signal, the intensities of the interference signal, and the correction values. For instance, the processing device 660 may determine the fourth corresponding relationship based on the first difference, the second difference, and the emulation intensity of each of the at least one emulation effective received signal. However, those variations and modifications may not depart from the protection of the present disclosure.

FIG. 11 is a diagram illustrating an exemplary computing device according to some embodiments of the present disclosure.

In some embodiments, a computing device 1100 is provided. The computing device 1100 may be a server, and its internal components may be shown in FIG. 11. The computing device 1100 may include a processor 1110, a storage, a network interface 1150, and a database 1133 connected through a system bus 1120. The processor 1110 of the computing device 1100 may be configured to provide computing and/or control capabilities. The storage of the computing device 1400 may include a non-volatile storage medium 1130 and an internal memory 1140. The non-volatile storage medium 1130 may store an operating system 1131, computer program(s) 1132, and the database 1133. The internal memory 1440 may provide an environment for the operation of the operating system 1131 and the computer program(s) 1132 of the non-volatile storage medium 1130. The database 1133 of the computing device 1100 may be configured to store data associated with time correction (e.g., the receiving time of the valid signal, the correction information, etc.). The network interface 1150 of the computing device 1100 may be configured to communicate with an external terminal through a network connection. The computer program(s) 1132 may be executed by the processor 1110 to implement the time correction.

It will be understood by those skilled in the art that the structure shown in FIG. 11 is merely a block diagram of a part of the structure related to the present disclosure, and does not constitute a limitation on the computing device to which the present disclosure scheme is applied. The computing device may include more or fewer components than those shown in the figures, or some components may be combined, or have different component arrangements.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended for those skilled in the art, though not expressly stated herein. These alterations, improvements, and modifications are intended to be suggested by the present disclosure, and are within the spirit and scope of the exemplary embodiments of the present disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, device, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A device configured for time correction in molecular imaging, the device comprising:
    a signal filter configured to obtain a valid signal and an interference signal by filtering an input signal;
    a first time measurement component configured to measure a receiving time of the valid signal;
    a correction component configured to collect correction information for correcting the receiving time of the valid signal; and
    a processing device configured to determine a corrected receiving time of the valid signal by correcting the receiving time of the valid signal based on the correction information, wherein to obtain a valid signal and an interference signal by filtering an input signal, the signal filter is configured to:
        generate a filtered input signal by performing a filtering operation on the input signal;
        extract a first portion of the filtered input signal as the interference signal, an amplitude of the first portion being larger than a first threshold and smaller than a second threshold; and
        extract a second portion of the filtered input signal as the valid signal, an amplitude of the second portion being larger than the second threshold, the second threshold being greater than the first threshold.

2. The device of claim 1, wherein the correction information includes a receiving time of the interference signal, and to determine a corrected receiving time of the valid signal, the processing device is configured to:
    determine a receiving time difference between the valid signal and the interference signal by comparing the receiving time of the interference signal and the receiving time of the valid signal;
    obtain a corresponding relationship between correction values and receiving time differences between the valid signal and the interference signal;
    determine a correction value based on the receiving time difference and the corresponding relationship; and
    determine the corrected receiving time of the valid signal by correcting the receiving time of the valid signal based on the correction value.

3. The device of claim 2, wherein the corresponding relationship is determined by performing a process including:
    generating at least one emulation effective received signal, wherein each of the at least one emulation effective received signal is generated by superposing an emulation interference signal on an emulation valid signal;
    for each of the at least one emulation effective received signal,
        determining a first difference between a receiving time of the corresponding emulation interference signal and a receiving time of the corresponding emulation effective received signal; and
        determining a second difference between a receiving time of the corresponding emulation valid signal and the receiving time of the corresponding emulation effective received signal;
    determining the corresponding relationship based on the first difference and the second difference of each of the at least one emulation effective received signal.

4. The device of claim 1, wherein the correction information includes an intensity of the interference signal, and to determine a corrected receiving time of the valid signal, the processing device is configured to:
    obtain a corresponding relationship between correction values and intensities of the interference signal;
    determine a correction value based on the intensity of the interference signal and the corresponding relationship; and
    determine the corrected receiving time of the valid signal by correcting the receiving time of the valid signal based on the correction value.

5. The device of claim 4, wherein the corresponding relationship is determined by performing a process including:
    generating at least one emulation effective received signal, wherein each of the at least one emulation effective received signal is generated by superposing an emulation interference signal on an emulation valid signal;
    for each of the at least one emulation effective received signal,
        determining an emulation intensity of the corresponding emulation interference signal; and
        determining a difference between a receiving time of the corresponding emulation effective received signal and a receiving time of the corresponding emulation valid signal;
    determining the corresponding relationship based on the emulation intensity and the difference of each of the at least one emulation effective received signal.

6. The device of claim 1, wherein the correction information includes an amplitude and a duration of a target portion of the valid signal.

7. The device of claim 6, wherein the target portion is a leading edge of the valid signal.

8. The device of claim 6, wherein the correction component includes:
    an amplitude measurement component configured to measure the amplitude of the target portion of the valid signal; and
    a second time measurement component configured to measure the duration of the target portion of the valid signal.

9. The device of claim 6, wherein to determine a corrected receiving time of the valid signal by correcting the receiving time of the valid signal based on the correction information, the processing device is configured to:
    determine a correlation coefficient between the amplitude and the duration;
    determine a correction value based on the correlation coefficient; and determine the corrected receiving time of the valid signal by correcting the receiving time of the valid signal based on the correction value.

10. The device of claim 1, further comprising a signal amplification component configured to:
   generate a first amplification signal by amplifying the valid signal and transmit the first amplification signal to the first time measurement component,
   generate a second amplification signal by amplifying the valid signal and transmit the second amplification signal to the correction component, wherein
   the first time measurement component measures the receiving time of the valid signal based on the first amplification signal, and the correction component collects the correction information based on the second amplification signal.

11. The device of claim 10, wherein the signal amplification component is electrically connected to a photoelectric conversion component, and
   the photoelectric conversion component is configured to receive an excitation signal and convert the excitation signal into the valid signal.

12. The device of claim 1, wherein the input signal is an input electrical signal.

13. The device of claim 1, wherein the correction component is configured to collect the correction information for correcting the receiving time of the valid signal based on the valid signal and the interference signal.

14. A positron emission tomography (PET) system, comprising:
   a detector module configured to detect a radiation photon emitted from a subject during a PET scan;
   a photoelectric conversion component configured to convert the radiation photon detected by the detector module into an input signal;
   a signal processing component configured to generate a valid signal by processing the input signal; and
   the device of claim 1 configured to determine a corrected receiving time of the valid signal.

15. The PET system of claim 14, wherein the signal processing component includes a signal filter configured to generate the valid signal by filtering the input signal.

16. A method configured for time correction in molecular imaging, implemented on a computing device having at least one processor and at least one storage device, the method comprising:
   obtaining a valid signal and an interference signal by filtering an input signal;
   measuring a receiving time of the valid signal;
   collecting correction information for correcting the receiving time of the valid signal; and
   determining a corrected receiving time of the valid signal by correcting the receiving time of the valid signal based on the correction information.

17. The method of claim 16, wherein the obtaining a valid signal and an interference signal by filtering an input signal comprises:
   generating a filtered input signal by performing a filtering operation on the input signal;
   extracting a first portion of the filtered input signal as the interference signal, an amplitude of the first portion being larger than a first threshold and smaller than a second threshold; and
   extracting a second portion of the filtered input signal as the valid signal, an amplitude of the second portion being larger than the second threshold, the second threshold being greater than the first threshold.

18. The method of claim 16, wherein the correction information includes a receiving time of the interference signal, and the determining a corrected receiving time of the valid signal comprises:
   determining a receiving time difference between the valid signal and the interference signal by comparing the receiving time of the interference signal and the receiving time of the valid signal;
   obtaining a corresponding relationship between correction values and receiving time differences between the valid signal and the interference signal;
   determining a correction value based on the receiving time difference and the corresponding relationship; and
   determining the corrected receiving time of the valid signal by correcting the receiving time of the valid signal based on the correction value.

* * * * *